(12) United States Patent
Kumar et al.

(10) Patent No.: US 8,501,926 B2
(45) Date of Patent: Aug. 6, 2013

(54) MALARIA VACCINE

(75) Inventors: Nirbhay Kumar, Potomac, MD (US);
Evelina Angov, Silver Spring, MD (US)

(73) Assignees: The Johns Hopkins University, Baltimore, MD (US); The United States of America, as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 13/120,784

(22) PCT Filed: Jul. 22, 2009

(86) PCT No.: PCT/US2009/004243
§ 371 (c)(1),
(2), (4) Date: Mar. 24, 2011

(87) PCT Pub. No.: WO2010/036293
PCT Pub. Date: Apr. 1, 2010

(65) Prior Publication Data
US 2011/0171266 A1    Jul. 14, 2011

Related U.S. Application Data

(60) Provisional application No. 61/099,651, filed on Sep. 24, 2008.

(51) Int. Cl.
*A61K 39/015* (2006.01)

(52) U.S. Cl.
USPC ...... 536/23.7; 435/243; 435/320.1; 435/69.3; 424/272.1

(58) Field of Classification Search
None
See application file for complete search history.

(56) References Cited

U.S. PATENT DOCUMENTS

| | | | |
|---|---|---|---|
| 5,502,168 A * | 3/1996 | Kumar | 530/388.4 |
| 5,753,238 A | 5/1998 | Kaslow et al. | |
| 5,798,106 A * | 8/1998 | Schoenmakers et al. | 424/272.1 |
| 6,316,000 B1 * | 11/2001 | Williamson et al. | 424/191.1 |
| 6,333,406 B1 * | 12/2001 | Inselburg et al. | 536/23.7 |
| 6,544,518 B1 * | 4/2003 | Friede et al. | 424/184.1 |
| 6,846,481 B1 * | 1/2005 | Gaertig et al. | 424/93.1 |

(Continued)

FOREIGN PATENT DOCUMENTS

| | | | |
|---|---|---|---|
| WO | 94/12640 | * | 6/1994 |
| WO | 03085114 A1 | | 10/2003 |

(Continued)

OTHER PUBLICATIONS

Milek, RLB et al, Vaccine, vol. 18, pp. 1402-1411, 2000, Assembly and expression of a synthetic gene encoding the antigen Pfs48/45 of the human malaria parasite *Plasmodium falciparum* in yeast.*

(Continued)

*Primary Examiner* — Albert Navarro
*Assistant Examiner* — Ginny Portner
(74) *Attorney, Agent, or Firm* — Johns Hopkins Technology Transfer

(57) ABSTRACT

The present invention features immunogenic compositions based on pre-fertilization or post-fertilization antigens expressed in the circulating gametocytes in the peripheral blood of infected persons or on the malaria parasites' stages of development in the mosquito midgut including extracellular male and female gametes, fertilized zygote and ookinete. The invention also features methods to prevent the transmission of malaria using the immunogenic compositions of the invention.

5 Claims, 8 Drawing Sheets

U.S. PATENT DOCUMENTS

| | | | |
|---|---|---|---|
| 6,958,235 B1 * | 10/2005 | Longacre-Andre et al. | 435/320.1 |
| 7,192,934 B1 * | 3/2007 | Kaslow et al. | 514/44 R |
| 7,407,658 B2 | 8/2008 | Kaslow et al. | |
| 7,696,308 B2 * | 4/2010 | Longacre-Andre et al. | 530/300 |
| 8,273,357 B2 * | 9/2012 | Hacohen et al. | 424/193.1 |
| 2003/0049278 A1 | 3/2003 | Kaslow et al. | |
| 2004/0137512 A1 * | 7/2004 | Horii | 435/7.1 |
| 2004/0242517 A1 * | 12/2004 | Cascalho et al. | 514/44 |
| 2005/0095256 A1 * | 5/2005 | Bujard et al. | 424/191.1 |
| 2005/0096288 A1 * | 5/2005 | Guevara, Jr. | 514/44 |
| 2005/0265974 A1 * | 12/2005 | Pau et al. | 424/93.2 |
| 2006/0088547 A1 | 4/2006 | Lanar et al. | |
| 2006/0105347 A1 * | 5/2006 | Meade et al. | 435/6 |
| 2006/0147477 A1 * | 7/2006 | Cabezon Siliva et al. | 424/277.1 |
| 2006/0233789 A1 * | 10/2006 | Endo et al. | 424/133.1 |
| 2007/0009994 A1 * | 1/2007 | Horii | 435/69.3 |
| 2007/0071726 A1 * | 3/2007 | Pau et al. | 424/93.2 |
| 2007/0269410 A1 * | 11/2007 | Tucker | 424/93.2 |
| 2009/0047303 A1 * | 2/2009 | Shaw et al. | 424/194.1 |
| 2010/0055167 A1 * | 3/2010 | Zhang et al. | 424/450 |
| 2010/0062028 A1 * | 3/2010 | Cohen et al. | 424/272.1 |

FOREIGN PATENT DOCUMENTS

| | | | |
|---|---|---|---|
| WO | 2004/055187 | * | 7/2004 |
| WO | 2005/025614 | * | 3/2005 |
| WO | 2006124712 A2 | | 11/2006 |

OTHER PUBLICATIONS

Octchkourov, NS et al, PNAS, Mar. 18, 2008, vol. 105(11), pp. 4301-4305, Correctly folded Pfs48/45 protein of *Plasmodium falciparum* elicits malaria transmission-blocking immunity in mice.*

Escalante, AA et al, Molecular and Biochemical Parasitology, vol. 119(1), pp. 17-22, Polymorphism in the gene encoding the Pfs48/45 antigen of *Plasmodium falciparum*. XI Asembo Bay Cohort Project.*

Milek et al., "Immunological properties of recombinant proteins of the transmission blocking vaccine candidate, Pfs48/45, of the human malaria parasite *Plasmodium falciparum* produced in *Escherichia coli*", Parasite Immunology, vol. 20, No. 8, pp. 377-385 (1998).

* cited by examiner

[MAHHHHHHPGGSGSGT] N$_{28}$NDF............TIDS$_{427}$
FIG. 1A
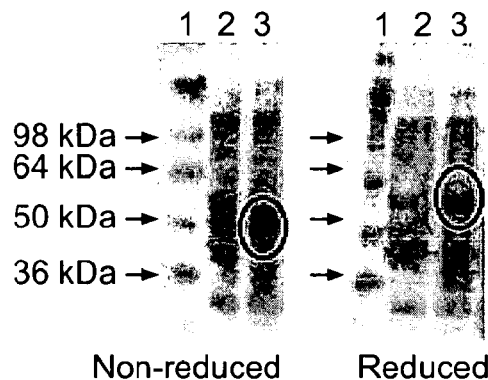
Non-reduced     Reduced
FIG. 1B
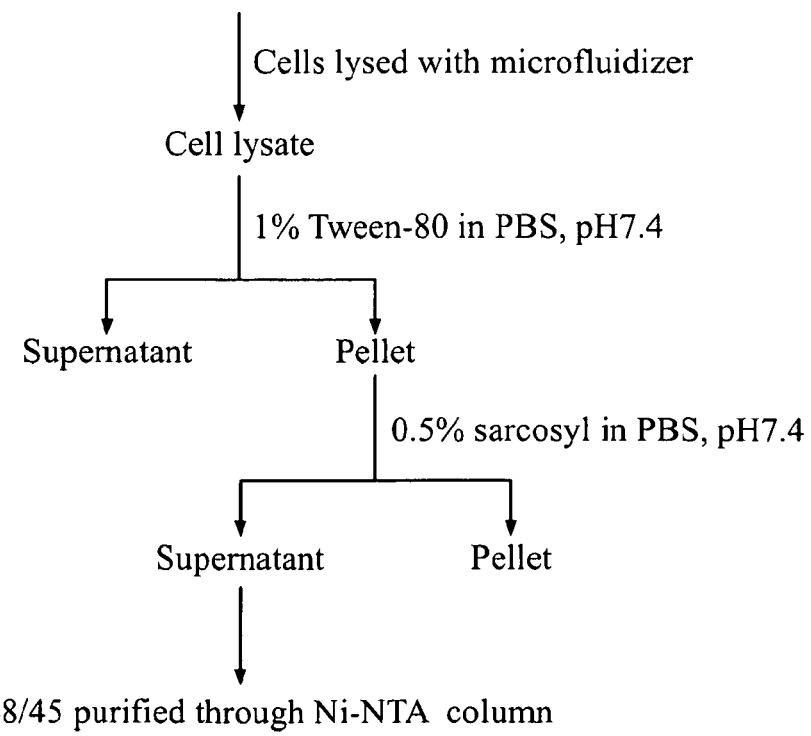
FIG. 1C

SEQUENCE LISTING

```
<160> NUMBER OF SEQ ID NOS: 16

<210> SEQ ID NO 1
<211> LENGTH: 400
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Asn Asn Asp Phe Tyr Asn Pro Ser Ala Leu Asn Ser Glu Ile Ser Gly
1               5                   10                  15

Phe Ile Gly Tyr Lys Cys Asn Phe Ser Asn Glu Gly Val His Asn Leu
            20                  25                  30

Lys Pro Asp Met Arg Glu Arg Ser Ile Phe Cys Asn Ile His Ser
        35                  40                  45

Tyr Phe Ile Tyr Asp Lys Ile Arg Leu Ile Ile Pro Lys Lys Ser Ser
    50                  55                  60

Ser Pro Glu Phe Lys Ile Leu Pro Glu Lys Cys Phe Gln Lys Val Tyr
```

```
                65                  70                  75                  80
Thr Asp Tyr Glu Asn Arg Val Glu Thr Asp Ile Ser Glu Leu Gly Leu
                    85                  90                  95
Ile Glu Tyr Glu Ile Glu Glu Asn Asp Thr Asn Pro Asn Tyr Asn Glu
                    100                 105                 110
Arg Thr Ile Thr Ile Ser Pro Phe Ser Pro Lys Asp Ile Glu Phe Phe
                    115                 120                 125
Cys Phe Cys Asp Asn Thr Glu Lys Val Ile Ser Ser Ile Glu Gly Arg
                    130                 135                 140
Ser Ala Met Val His Val Arg Val Leu Lys Tyr Pro His Asn Ile Leu
145                 150                 155                 160
Phe Thr Asn Leu Thr Asn Asp Leu Phe Thr Tyr Leu Pro Lys Thr Tyr
                    165                 170                 175
Asn Glu Ser Asn Phe Val Ser Asn Val Leu Glu Val Glu Leu Asn Asp
                    180                 185                 190
Gly Glu Leu Phe Val Leu Ala Cys Glu Leu Ile Asn Lys Lys Cys Phe
                    195                 200                 205
Gln Glu Gly Lys Glu Lys Ala Leu Tyr Lys Ser Asn Lys Ile Ile Tyr
                    210                 215                 220
His Asn Lys Leu Thr Ile Phe Lys Ala Pro Phe Tyr Val Thr Ser Lys
225                 230                 235                 240
Asp Val Asn Thr Glu Cys Thr Cys Lys Phe Lys Asn Asn Tyr Lys
                    245                 250                 255
Ile Val Leu Lys Pro Lys Tyr Glu Lys Lys Val Ile His Gly Cys Asn
                    260                 265                 270
Phe Ser Ser Asn Val Ser Ser Lys His Thr Phe Thr Asp Ser Leu Asp
                    275                 280                 285
Ile Ser Leu Val Asp Asp Ser Ala His Ile Ser Cys Asn Val His Leu
290                 295                 300
Ser Glu Pro Lys Tyr Asn His Leu Val Gly Leu Asn Cys Pro Gly Asp
305                 310                 315                 320
Ile Ile Pro Asp Cys Phe Phe Gln Val Tyr Gln Pro Glu Ser Glu Glu
                    325                 330                 335
Leu Glu Pro Ser Asn Ile Val Tyr Leu Asp Ser Gln Ile Asn Ile Gly
                    340                 345                 350
Asp Ile Glu Tyr Tyr Glu Asp Ala Glu Gly Asp Asp Lys Ile Lys Leu
                    355                 360                 365
Phe Gly Ile Val Gly Ser Ile Pro Lys Thr Thr Ser Phe Thr Cys Ile
                    370                 375                 380
Cys Lys Lys Asp Lys Lys Ser Ala Tyr Met Thr Val Thr Ile Asp Ser
385                 390                 395                 400

<210> SEQ ID NO 2
<211> LENGTH: 1200
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
aataacgact tctacaaccc atcggctctc aactctgaaa tcagcggctt catcggctac      60
aagtgcaact tcagcaacga aggcgttcac aacctgaagc cagacatgcg agaacgacgc     120
agcattttct gtaatataca ctcgtacttc atctacgaca agatccgtct gatcatccca     180
aaaaaaagct cgagcccaga gttcaaaatc ctgcctgaaa aatgcttcca gaaagtttac     240
```

```
actgactacg agaaccgtgt tgaaactgac atctcggaac tgggcctgat tgaatacgaa    300
atcgaagaaa acgacaccaa tccaaactac aacgaacgca ccatcacgat cagcccattc    360
tctccaaaag atattgaatt cttctgcttc tgcgacaaca ctgaaaaggt tatcagctct    420
atcgaagggc gttctgctat ggttcacgta cgagttctga ataccccaca caacattctg    480
ttcactaacc tgaccaacga cctcttcacc tacctcccta aaacctacaa cgaaagcaac    540
ttcgtttcta acgttctgga agttgaactg aacgacggcg aactgttcgt tctggcttgc    600
gaactcatta acaaaaaatg cttccaggaa ggcaaagaaa aagccctgta caaatctaac    660
aaaatcattt accacaacaa gctcactata ttcaaagctc cattctacgt taccagcaaa    720
gacgttaaca ccgaatgcac ctgtaaattc aaaaacaaca actacaaaat cgttctgaaa    780
ccaaaatacg aaaaaaaagt catccatggc tgcaattta gcagcaacgt atctagcaaa    840
cacactttca ccgactctct ggacattagc ctggttgacg actctgctca cattagctgc    900
aatgttcacc tcagcgaacc aaaatacaac cacctcgttg gcctgaactg cccaggcgac    960
attatcccag actgtttctt ccaggtttac cagccagaaa gcgaagaact cgaaccatcg   1020
aatattgttt acctggacag ccagatcaac atcggcgaca ttgaatacta cgaagacgct   1080
gaaggcgacg acaaaattaa actgttcggc atcgttggct ctatcccaaa aacgaccagc   1140
ttcacttgca tctgcaagaa ggacaaaaaa tctgcttaca tgaccgttac tatcgactct   1200
```

<210> SEQ ID NO 3
<211> LENGTH: 185
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Lys Tyr Asn Asn Ala Lys Val Thr Val Asp Thr Val Cys Lys Arg Gly
1               5                   10                  15

Phe Leu Ile Gln Met Ser Gly His Leu Glu Cys Lys Cys Glu Asn Asp
            20                  25                  30

Leu Val Leu Val Asn Glu Glu Thr Cys Glu Glu Lys Val Leu Lys Cys
        35                  40                  45

Asp Glu Lys Thr Val Asn Lys Pro Cys Gly Asp Phe Ser Lys Cys Ile
    50                  55                  60

Lys Ile Asp Gly Asn Pro Val Ser Tyr Ala Cys Lys Cys Asn Leu Gly
65                  70                  75                  80

Tyr Asp Met Val Asn Asn Val Cys Ile Pro Asn Glu Cys Lys Asn Val
                85                  90                  95

Thr Cys Gly Asn Gly Lys Cys Ile Leu Asp Thr Ser Asn Pro Val Lys
            100                 105                 110

Thr Gly Val Cys Ser Cys Asn Ile Gly Lys Val Pro Asn Val Gln Asp
        115                 120                 125

Gln Asn Lys Cys Ser Lys Asp Gly Glu Thr Lys Cys Ser Leu Lys Cys
    130                 135                 140

Leu Lys Glu Asn Glu Thr Cys Lys Ala Val Asp Gly Ile Tyr Lys Cys
145                 150                 155                 160

Asp Cys Lys Asp Gly Phe Ile Ile Asp Asn Glu Ser Ser Ile Cys Thr
                165                 170                 175

Ala Phe Ser Ala Tyr Asn Ile Leu Asn
            180                 185
```

<210> SEQ ID NO 4
<211> LENGTH: 555
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
aagtataaca acgccaaagt tactgtcgac actgtatgta acgtggtttt cctgattcaa      60
atgagcggcc acctcgaatg caaatgcgaa aacgacctgg tcctggtaaa cgaagaaacc     120
tgcgaagaaa aagtttttaaa atgcgatgaa aagactgtaa acaaaccgtg cggtgacttc     180
tcgaaatgca ttaaaattga cggtaaccct gtttcttatg cttgcaaatg caacctcggt     240
tacgacatgg taaacaacgt tgcattccg aacgaatgca gaacgtaac ttgcggcaat      300
ggcaaatgca ttctggacac ctcgaaccca gttaaaactg gtgtttgttc ttgcaacatt     360
gggaaagttc ctaacgtaca ggaccagaac aaatgctcta aagacggtga acgaaatgt      420
tctctgaaat gtctgaaaga aaacgaaacg tgcaaagctg ttgacggtat ttacaaatgc     480
gactgcaaag acggttttcat tattgacaac gaatcgagca tttgcactgc tttctctgct     540
tacaacattc tgaac                                                     555
```

<210> SEQ ID NO 5
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Leu Lys Arg Gln Leu Ala Asn Leu Leu Val Leu Ser Leu Leu
1               5                   10                  15

Arg Gly Ile Thr His Thr Gln Met Ala Lys Gly Glu Val Lys Tyr Val
                20                  25                  30

Pro Pro Glu Glu Leu Asn Lys Asp Val Ser Gly Phe Phe Gly Phe Lys
            35                  40                  45

Cys Asn Phe Ser Ser Lys Gly Val His Asn Leu Glu Pro Ile Leu Thr
        50                  55                  60

Glu Lys Arg Ser Leu Val Cys Ser Ile Tyr Ser Tyr Phe Ile Tyr Asp
65                  70                  75                  80

Lys Ile Lys Leu Thr Ile Pro Lys Lys Ile Pro Gly Ser Lys Phe Lys
                85                  90                  95

Met Leu Pro Glu Lys Cys Phe Gln Thr Val Tyr Thr Asn Tyr Glu Lys
            100                 105                 110

Arg Thr Glu Glu Lys Ile Glu Asn Met Gly Leu Val Glu Tyr Glu Val
        115                 120                 125

Lys Glu Asp Asp Ser Asn Ser Glu Tyr Thr Glu Lys Ile Leu Thr Ile
    130                 135                 140

Ser Pro Phe Asn Thr Lys Asp Val Glu Phe Phe Cys Ile Cys Asp Asn
145                 150                 155                 160

Ser Glu Asn Val Ile Ser Asn Val Lys Gly Arg Val Ala Leu Val Gln
                165                 170                 175

Val Asn Val Leu Lys Tyr Pro His Lys Ile Thr Ser Ile Asn Leu Thr
            180                 185                 190

Lys Glu Pro Tyr Ser Tyr Leu Pro Asn Gln Val Asp Lys Thr Ser Phe
        195                 200                 205

Lys Ser His Lys Leu Asp Leu Glu Leu Gln Asp Gly Glu Leu Val Val
    210                 215                 220

Leu Ala Cys Glu Lys Val Asp Asp Lys Cys Phe Lys Lys Gly Lys Asp
225                 230                 235                 240

Thr Ser Pro Leu Ser Leu Tyr Lys Ser Lys Ile Val Tyr His Lys
            245                 250                 255

Asn Leu Ser Ile Phe Lys Ala Pro Val Tyr Val Lys Ser Ala Asp Val
        260                 265                 270

Thr Ala Glu Cys Ser Cys Asn Val Asp Ser Thr Ile Tyr Thr Leu Ser
    275                 280                 285

Leu Lys Pro Val Tyr Thr Lys Lys Leu Ile His Gly Cys Asn Phe Ser
    290                 295                 300

Ser Asp Lys Ser Thr His Asn Phe Thr Asn His Val Asp Met Ala Glu
305                 310                 315                 320

Leu Gly Glu Asn Ala Gln Ile Thr Cys Ser Ile Glu Leu Val Asp Thr
                325                 330                 335

Ser Tyr Asn His Leu Ile Gly Met Ser Cys Pro Gly Glu Val Leu Pro
            340                 345                 350

Glu Cys Phe Phe Gln Val Tyr Gln Arg Glu Ser Pro Glu Leu Glu Pro
        355                 360                 365

Ser Lys Ile Val Tyr Leu Asp Ala Gln Leu Asn Ile Gly Asn Val Glu
    370                 375                 380

Tyr Phe Glu Asp Ser Lys Gly Glu Asn Ile Val Lys Ile Phe Gly Leu
385                 390                 395                 400

Val Gly Ser Ile Pro Lys Thr Thr Ser Phe Thr Cys Ile Cys Arg Lys
                405                 410                 415

Gly Lys Lys Ile Gly Tyr Met Ser Val Lys Ile Ala Ala Gly Tyr Phe
            420                 425                 430

Gly Phe Leu Ala Lys Ile Phe Ile Leu Leu Ile Val Leu Leu Leu Leu
        435                 440                 445

Tyr Phe
    450

<210> SEQ ID NO 6
<211> LENGTH: 1274
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
catatggcac accatcatca tcatcatccc gggggatccg gttctggtac catggccaag      60
ggcgaggtca atatgtgcc tccagaggag ctgaataagg atgtgagcgg cttttttggg     120
tttaagtgta attttagcag caagggcgtc cataacctcg agcctattct gacgagaag     180 cgaagcctgg tctgtagcat ttatagctat tttatttatg ataagattaa actgacgatt     240
cctaaaaaaa ttccaggctc gaagtttaag atgctcccag agaagtgttt tcaaacggtg     300
tatactaatt atgagaagcg cacggaggag aagattgaga atatgggcct cgtggagtat     360
gaggtgaagg aggatgatag caactcggag tatacggaga agattctgac gattagccct     420
tttaacacga agatgtgga gttttttttgt atttgtgata actcggagaa cgtcattagc     480
aatgtgaaag gccgagtggc gctcgtgcaa gtgaatgtgc tcaagtatcc tcataagatt     540
acgagcatta acctgacgaa agagccatat tcgtatctgc ctaatcaagt ggataaaacg     600

```
agctttaagt cgcataagct cgatctcgag ctccaagatg gcgagctcgt ggtgctcgcg    660
tgtgagaagg tggatgataa gtgttttaag aaaggcaaag atactagccc actgagcctc    720
tataaaagca agaagattgt gtatcataaa aacctcagca ttttttaaggc gcctgtgtat   780 gtgaagagcg ccgatgtgac ggcggagtgt agctgtaatg tggatagcac gatttatact    840
ctcagcctca agcctgtgta tacgaagaaa ctcattcatg ggtgtaattt tagctcggat    900
aagagcacgc ataattttac taatcatgtg gatatggccg agctggggga gaatgcgcaa    960
attacgtgta gcattgagct cgtggatacg agctataatc atctcattgg catgagctgt   1020
cctggggagg tgctgcctga gtgttttttt caagtgtatc aacgagagag cccagagctc   1080
gagcctagca agattgtcta tctcgatgcc caactcaata ttggcaatgt ggagtatttt   1140
gaggatagca aaggcgagaa tattgtgaag attttttgggc tcgtgggcag cattcctaag   1200
acgacgagct ttacgtgtat ttgtcgaaaa gggaaaaaga ttgggtatat gagcgtgaag   1260
tgataagcgg ccgc                                                      1274

<210> SEQ ID NO 7
<211> LENGTH: 1347
<212> TYPE: DNA
<213> ORGANISM: Plasmodium falciparum

<400> SEQUENCE: 7
atgatgttat atatttctgc gaaaaaggct caagttgctt tcatcttata tatagtattg     60
gtattaagaa taataagtgg aaacaatgat ttttataatc ctagcgcttt gaatagtgaa    120
atatctggat ttataggata taagtgtaat ttttcaaatg aaggtgttca taatttaaag    180
ccagatatgc gtgaacgtag gtctattttt tgcaacatcc attcgtattt tatatatgat    240
aagataagat taataatacc taaaaaaagt tcgtcacctg agtttaaaat attacccgaa    300
aaatgttttc aaaaagtata tactgattat gagaatagag ttgaaactga tatatcggaa    360
ttaggtttaa ttgaatatga aatagaagaa atgatacaa accctaatta taatgaaagg    420
acaataacta tatctccatt tagtccaaaa gacattgaat ttttttgttt ttgtgataat    480
actgaaaagg ttatatcaag tatagaaggg agaagtgcta tggtacatgt acgtgtatta    540
aaatatccac ataatatttt atttactaat ttaacaaatg atcttttttac atatttgccg    600 aaaacatata atgaatctaa ttttgtaagt aatgtattag aagtagaatt aaatgatgga    660
gaattatttg ttttagcttg tgaactaatt aataaaaaat gttttcaaga aggaaaagaa    720
aaagccttat ataaaagtaa taaaataatt tatcataata agttaactat ctttaaagct    780
ccattttatg ttacatcaaa agatgttaat acagaatgta catgcaaatt taaaaataat    840
aattataaaa tagtttttaaa accaaaatat gaaaaaaaag tcatacacgg atgtaacttc    900
tcttcaaatg ttagttctaa acatactttt acagatagtt tagatatttc tttagttgat    960
gatagtgcac atatttcatg taacgtacat ttgtctgaac caaatataaa tcatttggta   1020
ggtttaaatt gtcctggtga tattatacca gattgctttt ttcaagtata tcaacctgaa   1080
tcagaagaac ttgaaccatc caacattgtt tatttagatt cacaaataaa tataggagat   1140
attgaatatt atgaagatgc tgaaggagat gataaaatta aattatttgg tatagttgga   1200
agtataccaa aaacgacatc ttttacttgt atatgtaaga aggataaaaa aagtgcttat   1260
atgacagtta ctatagattc agcatattat ggatttttgg ctaaaacatt tatattccta   1320
attgtagcaa tattattata tatttag                                       1347

<210> SEQ ID NO 8
```

-continued

<211> LENGTH: 620
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

| catatggcac accatcatca tcatcatccc gggggatccg gttctggtac caagtataac | 60 |
| aacgccaaag ttactgtcga cactgtatgt aaacgtggtt cctgattca aatgagcggc | 120 |
| cacctcgaat gcaaatgcga aaacgacctg gtcctggtaa acgaagaaac ctgcgaagaa | 180 |
| aaagttttaa aatgcgatga aaagactgta acaaaccgt gcggtgactt ctcgaaatgc | 240 |
| attaaaattg acggtaaccc tgtttcttat gcttgcaaat gcaacctcgg ttacgacatg | 300 |
| gtaaacaacg tttgcattcc gaacgaatgc aagaacgtaa cttgcggcaa tggcaaatgc | 360 |
| attctggaca cctcgaaccc agttaaaact ggtgtttgtt cttgcaacat gggaaagtt | 420 |
| cctaacgtac aggaccagaa caaatgctct aaagacggtg aaacgaaatg ttctctgaaa | 480 |
| tgtctgaaag aaaacgaaac gtgcaaagct gttgacggta tttacaaatg cgactgcaaa | 540 |
| gacggtttca ttattgacaa cgaatcgagc atttgcactg ctttctctgc ttacaacatt | 600 |
| ctgaactgat aagcggccgc | 620 |

<210> SEQ ID NO 9
<211> LENGTH: 1265
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

| catatggcac accatcatca tcatcatccc gggggatccg gttctggtac caataacgac | 60 |
| ttctacaacc catcggctct caactctgaa atcagcggct tcatcggcta caagtgcaac | 120 |
| ttcagcaacg aaggcgttca aacctgaag ccagacatgc gagaacgacg cagcattttc | 180 |
| tgtaatatac actcgtactt catctacgac aagatccgtc tgatcatccc aaaaaaaagc | 240 |
| tcgagcccag agttcaaaat cctgcctgaa aaatgcttcc agaaagttta cactgactac | 300 |
| gagaaccgtg ttgaaactga catctcggaa ctgggcctga ttgaatacga aatcgaagaa | 360 |
| aacgacacca atccaaacta caacgaacgc accatcacga tcagcccatt ctctccaaaa | 420 |
| gatattgaat tcttctgctt ctgcgacaac actgaaaagg ttatcagctc tatcgaaggg | 480 |
| cgttctgcta tggttcacgt acgagttctg aaatacccac acaacattct gttcactaac | 540 |
| ctgaccaacg acctcttcac ctacctccct aaaacctaca cgaaagcaa cttcgtttct | 600 |
| aacgttctgg aagttgaact gaacgacggc gaactgttcg ttctggcttg cgaactcatt | 660 |
| aacaaaaaat gcttccagga aggcaaagaa aaagccctgt acaaatctaa caaaatcatt | 720 |
| taccacaaca agctcactat attcaaagct ccattctacg ttaccagcaa agacgttaac | 780 |
| accgaatgca cctgtaaatt caaaacaac aactacaaaa tcgttctgaa accaaaatac | 840 |
| gaaaaaaaag tcatccatgg ctgcaatttt agcagcaacg tatctagcaa acacactttc | 900 |
| accgactctc tggacattag cctggttgac gactctgctc acattagctg caatgttcac | 960 |
| ctcagcgaac aaaatacaa ccacctcgtt ggcctgaact gcccaggcga cattatccca | 1020 |
| gactgtttct tccaggttta ccagccagaa agcgaagaac tcgaaccatc gaatattgtt | 1080 |
| tacctggaca gccagatcaa catcggcgac attgaatact acgaagacgc tgaaggcgac | 1140 |

-continued

| | |
|---|---|
| gacaaaatta aactgttcgg catcgttggc tctatcccaa aaacgaccag cttcacttgc | 1200 |
| atctgcaaga aggacaaaaa atctgcttac atgaccgtta ctatcgactc ttgataagcg | 1260 |
| gccgc | 1265 |

<210> SEQ ID NO 10
<211> LENGTH: 1699
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

| | |
|---|---|
| catatggcac accatcatca tcatcatccc gggggatccg gttctggtac caaagaatat | 60 |
| gtttgcgctt caccgaccag ctgaaaccga ccgaatctgg cccaaaagtt aaaaaatgcg | 120 |
| aagttaaagt taacgagccg ctgatcaaag ttaaaatcat ctgcccgctg aaaggcagcg | 180 |
| ttgaaaaact gtacgacaac atcgaatacg ttccaaaaaa atcgccgtac gttgttctga | 240 |
| ccaaagagga aactaaactc aaggaaaaac tgttgtcgaa actcatttac ggcctgctga | 300 |
| tcagccctac ggttaatgaa aaggagaaca acttcaaaga aggcgttatt gaattcactc | 360 |
| tgcctccagt ggttcataag gctaccgtgt tctacttcat ctgcgacaac agcaaaaccg | 420 |
| aagacgacaa taaaaaaggc aaccgtggga ttgttgaagt gtacgttgaa ccgtacggca | 480 |
| acaaaattaa cggctgcgct tttctcgacg aagacgaaga agaagaaaaa tacggcaacc | 540 |
| agattgaaga agacgaacac aacgagaaga tcaaaatgaa aacctttttc acgcaaaaca | 600 |
| tctacaaaaa aaacaacatc tacccgtgct acatgaaact gtactcgggc gacatcggcg | 660 |
| gcattctctt cccaaagaac atcaaaagca ccacgtgctt cgaagagatg atcccataca | 720 |
| acaaagaaat caaatggaac aaagaaaaca atctctgggg caatctggtt aacaacagcg | 780 |
| ttgtttacaa caaagagatg aacgctaaat acttcaacgt tcaatacgtt catattccaa | 840 |
| cctcttacaa agacaccctg aacctgttct gctctattat cctgaaagaa gaggaatcta | 900 |
| acctgattag cactagctac ctggtttacg tttctattaa cgaagaactg aacttcagcc | 960 |
| tctttgactt ctacgaaagc ttcgttccaa tcaaaaaaac gatccaggtt gctcagaaga | 1020 |
| acgttaacaa caaagaacac gactacacct gcgacttcac ggacaaactg acaaaacgg | 1080 |
| ttccaagcac tgctaacggg aagaaactgt tcatctgccg taagcacctg aaagaattcg | 1140 |
| acaccttcac gctgaaatgc aacgttaaca aaacccagta cccgaacata gagatcttcc | 1200 |
| caaaaaccct gaaagacaaa aaggaagttc tgaaactgga cctcgacatc cagtaccaga | 1260 |
| tgttctctaa attcttcaaa tttaacaccc aaaacgctaa gtacctgaac ctgtaccggt | 1320 |
| actacctgat tttcccgttc aaccacatcg gcaaaaaaga actgaaaaac aacccaacct | 1380 |
| acaaaaacca caaagacgtg aaatacttcg agcagagcag cgttctgagc cctctgagct | 1440 |
| cggctgattc tctggggaaa ctgctgaact tcctggacac tcaggagacg gtttgcctca | 1500 |
| cggaaaagat ccgttacctg aacctgtcta taaacgagct gggcagcgac aacaacacct | 1560 |
| tcagcgttac cttccaagtt ccgccgtaca tcgacattaa ggaaccattc tacttcatgt | 1620 |
| tcggctgcaa caacaacaaa ggcgaaggga acataggcat tgttgaactg ctgatcagca | 1680 |
| agcagtgata agcggccgc | 1699 |

<210> SEQ ID NO 11
<211> LENGTH: 1964
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11

```
catatggcac accatcatca tcatcatccc gggggatccg gttctggtac ccacgactac      60
acctgcgact tcacggacaa actggacaaa acggttccaa gcactgctaa cgggaagaaa     120
ctgttcatct gccgtaagca cctgaaagaa ttcgacacct tcacgctgaa atgcaacgtt     180
aacaaaaccc agtacccgaa catagagatc ttcccaaaaa ccctgaaaga caaaaaggaa     240
gttctgaaac tggacctcga catccagtac cagatgttct ctaaattctt caaatttaac     300
acccaaaacg ctaagtacct gaacctgtac ccgtactacc tgattttccc gttcaaccac     360
atcggcaaaa aagaactgaa aaacaaccca acctacaaaa accacaaaga cgtgaaatac     420
ttcgagcaga gcagcgttct gagccctctg agctcggctg attctctggg gaaactgctg     480
aacttcctgg acactcagga acggtttgc ctgacgaaa agatccgtta cctgaacctg      540
tctataaacg agctgggcag cgacaacaac accttcagcg ttaccttcca gttccgccg     600
tacatcgaca ttaaggaacc attctacttc atgttcggct gcaacaacaa caaaggcgaa     660
gggaacatag gcattgttga actgctgatc agcaagcagg aagaaaagat taaaggctgc     720
aactttcacg aaagcaaact ggactacttt aacgaaaata ttagctctga cacccacgaa     780
tgcaccctcc acgcttacga aaacgacatc attggcttca actgcctgga aactactcac     840
ccaaacgagg ttgaggttga agttgaagac gctgaaatct acctccagcc agagaactgc     900
ttcaacaacg tttacaaagg cctcaacagc gttgacatta ctactatcct gaaaaacgct     960
cagacctaca acatcaacaa caagaaaacc ccaacgttcc tgaaaattcc gccgtacaac    1020
ctgctggaag acgtcgaaat tcttgtcag tgcactatta acaggttgt taaaaaaatc     1080
aaagttatta tcacgaaaaa cgacaccgtt ctgctgaaac gtgaagtgca gagcgagagc    1140
accctggacg acaaaatcta caatgcgaa cacgaaaact tcattaaccc gcgtgttaac    1200
aaaaccttcg acgaaaacgt tgaatacacc tgcaacatca aaatcgagaa cttttcaac    1260
tacattcaga tcttctgccc ggccaaagac ctcggcattt acaaaaacat ccagatgtac    1320
tacgacattg ttaaaccgac ccgtgttccg cagttcaaaa aattcaacaa cgaagaactg    1380
cacaaactga ttccaaacag cgaaatgctg cacaaaacca agaaatgct gattctgtac    1440
aacgaagaaa aagtggacct cctgcacttc tacgttttc tgccgatcta catcaaagat    1500
atctacgaat ttaacatcgt ttgcgacaac agcaaaacca tgtggaaaaa ccagctgggc    1560
ggcaaagtta tctaccacat tactgttagc aaacgtgagc aaaaagttaa aggctgcagc    1620
ttcgacaacg aacacgctca catgttctct tacaacaaaa ctaacgttaa aaactgcatt    1680
atcgacgcta aaccaaaaga cctcatcggc tttgtttgcc ctagcggcac gctgaaactg    1740
accaactgct tcaaagacgc tatcgttcac accaacctga ccaacattaa cggcatcctc    1800
tacctgaaaa acaacctcgc taatttcacc tacaaacacc agttcaacta catggaaatc    1860
ccggctctga tggacaacga catcagcttc aaatgcatct gcgttgacct gaaaaaaaaa    1920
aaatacaacg tcaaaagccc gctgggccca tgataagcgg ccgc                    1964
```

<210> SEQ ID NO 12
<211> LENGTH: 2105
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12

```
catatggcac accatcatca tcatcatccc gggggatccg gttctggtac caaccgtcac      60
gtttgcgact ttagcaaaaa caacctgatt gttccggaaa gcctgaaaaa aaaagaagag     120
ctcggcggca acccggttaa cattcactgc tacgctctgc tgaaaccact ggacaccctg     180
tacgttaaat gcccaaccag caaagacaac tacgaagctg ctaaagttaa tatcagcgaa     240
aatgataacg aatacgagct gcaggttatc agcctgatag aaaaacgttt ccacaacttc     300
gagacgctgg aatcgaagaa accaggcaac ggcgacgttg ttgttcacaa cggcgttgtt     360
gacactggcc cagttctgga caattctacc ttcgaaaaat acttcaaaaa catcaaaatc     420
aaaccggaca aattcttcga gaaagttatc aacgaatacg acgacactga agaagaaaaa     480
gacctggaat ctatcctgcc aggggctatt gtttctccaa tgaaagttct gaaaaaaaag     540
gacccattca ccagctacgc tgctttcgtt gttccgccga ttgttcctaa agacctgcac     600
ttcaaagttg aatgcaacaa caccgaatac aaagacgaaa accagtacat ctctggctac     660
aacggcatca tccacattga catcagcaac tctaaccgca aaattaacgg ctgcgacttt     720
agcactaata actctagcat tctgacctcg tctgttaaac tggttaacgg cgaaactaaa     780
aactgcgaaa tcaacatcaa caacaacgaa gttttcggca taatctgcga caacgaaacc     840
aacctggacc cggaaaaatg cttccacgaa atctactcta agacaacaa aactgttaaa     900
aaattccgag aagttatccc aaacatcgac atctttagcc tgcacaacag caacaagaaa     960
aaagttgctt acgctaaagt tccactggac tacattaaca aactgctgtt cagctgcagc    1020
tgcaaaacca gccacactaa caccatcggc acgatgaaag ttactctcaa caaagacgaa    1080
aaagaagaag aagacttcaa aaccgctcag gcattaaac acaacaacgt tcacctgtgc    1140
aactttttcg acaacccaga actgaccttc gacaacaaca aaatcgttct gtgcaaaata    1200
gacgctgaat tatttagcga agttattatc cagctgccga tcttcggcac caagaacgtt    1260
gaagaaggcg ttcagaacga agaatacaaa aaattcagcc tgaaaccgag cctggttttc    1320
gacgacaata caacgacat taaagttatc ggcaaagaaa aaaacgaagt tagcatttct    1380
ctggctctca aaggggttta cggcaaccga attttcactt tcgacaaaaa cggcaaaaaa    1440
ggcgaaggca tttctttctt catcccaccg atcaaacagg acaccgacct gaaattcatc    1500
attaacgaaa ccatcgacaa cagcaacatt aaacagcgtg gcctgatcta cattttcgtt    1560
cgcaaaaacg ttagcgaaaa cagcttcaaa ctgtgcgact taccaccgg ctcgactagc    1620
ctgatggaac tgaactctca ggttaaagaa aaaagtgta ctgttaaaat taaaaaaggc    1680
gacattttcg gcctcaaatg cccaaaaggc ttcgctatct tcccgcaggc ttgcttctct    1740
aacgttctgc tggaatacta caatctgac tacgaagact ctgaacacat taactactac    1800
attcacaaag acaaaaaata caacctgaaa ccaaaagacg ttattgaact gatggacgaa    1860
aacttccgtg aactgcagaa catccagcag tacaccggca tcagcaacat taccgacgtg    1920
ctgcacttta aaaacttcaa cctgggcaac ctcccgctga acttcaaaaa ccactacagc    1980
accgcttacg ctaaagttcc ggacacgttc aacagcatta ttaattttag ctgcaactgc    2040
tacaacccgg aaaaacacgt ttacggcact atgcaggttg agagcgacaa ctgataagcg    2100
gccgc                                                                2105
```

<210> SEQ ID NO 13
<211> LENGTH: 2039
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

| | | | | | |
|---|---|---|---|---|---|
| catatggcac | accatcatca | tcatcatccc | ggggatccg | gttctggtac | caacgaacac | 60 |
| atctgcgact | acgaaaaaaa | cgaaagctta | atcagcaccc | tgccaaacga | caccaaaaaa | 120 |
| atccagaaat | ctatatgcaa | aattaacgct | aaagctctgg | acgttgttac | cattaaatgc | 180 |
| ccacacacca | aaaacttcac | gccaaaagac | tacttcccaa | acagcagcct | gatcactaac | 240 |
| gacaaaaaaa | ttgtgattac | tttcgacaag | aaaaacttcg | ttacttacat | cgacccaacc | 300 |
| aaaaaaacct | tcagcctcaa | agacatctac | atccagtctt | tctacggcgt | tagcctcgac | 360 |
| cacctcaacc | agatcaaaaa | aatccacgaa | gaatgggacg | acgttcacct | gttctaccca | 420 |
| ccacacaacg | ttctgcacaa | cgttgttctc | aacaaccaca | tcgtcaatct | gagcagcgct | 480 |
| ctggaaggcg | tcctgttcat | gaaaagcaaa | gttactggcg | acgaaaccgc | taccaaaaaa | 540 |
| aatactaccc | tcccgactga | cggcgttagc | tctattctga | ttccgccgta | cgttaaggaa | 600 |
| gacatcacct | tccacctctt | ctgcgggaaa | agcaccacca | aaaaaccgaa | taaaaagaat | 660 |
| accagcctcg | ctctcattca | catccacatc | agcagcaatc | gtaacattat | tcacggctgc | 720 |
| gactttctgt | acctggaaaa | ccagaccaac | gacgctattt | ctaacaacaa | caacaacagc | 780 |
| tacagcatct | tcacccacaa | caaaaacacc | gagaacaacc | tcatctgcga | catcagcctg | 840 |
| attccgaaaa | ctgttatcgg | cattaaatgc | ccaaacaaaa | aactgaaccc | gcagacctgc | 900 |
| ttcgacgaag | tgtactacgt | taaacaggaa | gacgttccat | cgaaaactat | caccgctgac | 960 |
| aaatacaaca | ccttctctaa | agataaaatc | ggcaacatcc | tgaaaaacgc | tataagcatt | 1020 |
| aacaacccgg | acgaaaagga | caacacctac | acttacctga | tcctgccgga | aaaattcgaa | 1080 |
| gaagaactga | tagacacgaa | aaaagttctg | gcttgcacct | gcgacaacaa | atacatcatc | 1140 |
| cacatgaaaa | tcgaaaaatc | taccatggac | aaaatcaaaa | tcgacgaaaa | aaaaaccatt | 1200 |
| ggcaaagaca | tctgcaaata | cgacgttact | actaaagttg | ctacttgcga | aattattgac | 1260 |
| accattgact | cgagcgttct | gaaagaacac | cacaccgttc | actacagcat | taccctgagc | 1320 |
| cgttgggaca | aactcattat | taaatacccg | accaacgaga | aaacccactt | tgaaaacttc | 1380 |
| ttcgttaacc | cattcaacct | gaaagacaaa | gttctgtaca | actacaacaa | accgatcaac | 1440 |
| atcgaacaca | tactgccggg | cgccattacc | accgacatct | acgacacgcg | taccaaaatt | 1500 |
| aaacagtaca | tcctgcgtat | tccgccgtac | gttcacaaag | acatccactt | tagcctggaa | 1560 |
| ttcaataact | cgctctctct | gaccaaacag | aaccagaaca | ttatttacgg | caacgttgcc | 1620 |
| aaaattttca | ttcacatcaa | ccagggctac | aaagaaattc | acggctgcga | ctttaccggc | 1680 |
| aaatactcgc | acctgttcac | ctacagcaaa | aaaccactgc | cgaacgacga | cgacatctgc | 1740 |
| aacgttacta | tcggcaacaa | caccctttagc | ggcttcgctt | gtctgtcgca | cttcgaactg | 1800 |
| aaaccgaaca | attgttttag | cagcgtttac | gactacaacg | aagccaacaa | agttaaaaaa | 1860 |
| ctgtttgacc | tctcgaccaa | agttgaactg | gatcacataa | aacagaacac | tagcggctac | 1920 |
| accctcagct | acattatttt | caacaaagaa | tcgaccaaac | tcaaatttag | ctgcacctgt | 1980 |
| agctcgaatt | acagcaacta | cactatccga | ataaccttcg | acccatgata | agcggccgc | 2039 |

<210> SEQ ID NO 14
<211> LENGTH: 6
<212> TYPE: PRT
<213> ORGANISM: Artificial Sequence
<220> FEATURE:

-continued

```
<223> OTHER INFORMATION: Description of Artificial Sequence: Synthetic
      6xHis tag

<400> SEQUENCE: 14

His His His His His His
1               5

<210> SEQ ID NO 15
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Met Ala His His His His His His Pro Gly Gly Ser Gly Ser Gly Thr
1               5                   10                  15

Asn Asn Asp Phe
            20

<210> SEQ ID NO 16
<211> LENGTH: 4
<212> TYPE: PRT
<213> ORGANISM: Plasmodium falciparum

<400> SEQUENCE: 16

Thr Ile Asp Ser
1
```

MALARIA VACCINE

CROSS-REFERENCE TO RELATED APPLICATIONS

This application is a 35 U.S.C. §371 U.S. national entry of International Application PCT/US2009/004243 (WO 2010/036293) having an International filing date of Jul. 22, 2009 which claims the benefit of U.S. Provisional Application No. 61/099,651, which was filed on Sep. 24, 2008, the entire contents of which are incorporated herein by reference.

BACKGROUND OF THE INVENTION

Malaria is one of most dangerous infectious diseases in tropical and subtropical countries, afflicting about 300 million people. The pathogen of the disease is a protozoan parasite, *Plasmodium* sp. which is transmitted by *Anopheles* mosquitoes. Four species of malaria parasites can infect humans under natural conditions: *Plasmodium falciparum, P. vivax, P. ovale,* and *P. malariae. P. falciparum* and *P. vivax* cause the most infections worldwide.

*P. falciparum* is the agent of severe, potentially fatal malaria. Malaria caused by *P. falciparum* is responsible for nearly 1 million deaths annually. Based on recent estimates from the WHO, worldwide, there were an estimated 247 million malaria cases among 3.3 billion people at risk living in 109 countries [1]. Infections caused by *P. falciparum* and *P. vivax* account for more than 90% of global malaria burden; the former being responsible for nearly all the deaths due to malaria, nearly a million deaths of children under 5 years [2]. Among the current efforts against malaria include increasing use of insecticide treated bed nets and use of combination drugs to tackle the problem associated with drug resistance. The emergence of drug-resistant strains over the last 4 decades has underscored the necessity for improved control strategies. Accordingly, the development of a safe and effective malaria vaccine will be an important step towards controlling malaria. Vaccine development efforts to date have focused on candidate antigens represented in the pre-erythrocytic, erythrocytic and sexual stages of the parasite. Currently, the only vaccine advanced in clinical development, RTS,S, has shown partial protection against infection and disease severity in several clinical trials [6,7].

Immunity against the sexual stages of the parasite offers an effective way to reduce or stop malaria transmission and in that respect offers the greatest promise towards the goal of progressively eliminating malaria from endemic countries. A transmission blocking vaccine (TBV) [8] specifically targeting the sexual development of the parasite in the mosquito vector may elicit immunity which can effectively block transmission of the parasite from invertebrate mosquito vector to vertebrate host. Transmission of malaria depends upon the presence of infectious male and female gametocytes in the peripheral blood of infected persons and successful ingestion of these gametocytes by *Anopheles* mosquitoes. Soon after ingestion, exflagellation occurs within the mosquito midgut, and emergent male gametes fertilize female gametes, resulting in the formation of zygotes. The zygotes undergo post-fertilization transformation into motile ookinetes which traverse the midgut epithelium and develop into oocysts resulting in the production of infective sporozoites. Finally the sporozoites are released into the hemocoel, invade the salivary glands and are transmitted to vertebrate hosts during subsequent blood feeding [9].

The targets of transmission blocking antibodies include pre-fertilization antigens (Pfs230 and Pfs48/45) expressed in the circulating gametocytes and post-fertilization antigens (Pfs25 and Pfs28) expressed during mosquito stage ookinete development [10]. Unlike Pfs25 and Pfs28, pre-fertilization antigens are also targets of the natural immune response and thus immunity induced by a vaccine based on any of these antigens will have the added benefit of natural boosting of immunity. To date, only Pfs25 and Pvs25 (*P. vivax* homolog of Pfs25) have undergone limited Phase I clinical trials with marginal success [11,12]. It has not been possible to evaluate any of the pre-fertilization antigens as vaccines simply because they have not been available in sufficient quantity and proper protein conformation.

Although much progress has been made in the recent past, the development of a safe, effective and affordable malaria vaccine has remained a challenge. A vaccine targeting sexual stages of the parasite will not only reduce malaria transmission by female *Anopheles* mosquitoes, but also reduce the spread of parasites able to evade immunity elicited by vaccines targeting pre-erythrocytic and erythrocytic asexual stages.

SUMMARY OF THE INVENTION

As described below, the present invention features immunogenic compositions based on pre-fertilization antigens expressed in the circulating gametocytes in the peripheral blood of infected persons. The present invention makes use of an approach that harmonizes codon usage frequency of the target gene with those of the expression host for heterologous expression of protein. Taking these concepts into account, an algorithm termed "codon harmonization" [19] was developed where synonymous codons from *E. coli* were selected that closely resemble the codon usage of a native pre-fertilization gene, for example the native Pfs48/45 gene, including regions coding 'link/end' segments of proteins in *P. falciparum.*

Also featured in the invention are antibodies, and methods to prevent the transmission of malaria using the immunogenic compositions of the invention.

In a first aspect, the invention features a method of blocking transmission of *Plasmodium falciparum* or *Plasmodium vivax* in a subject comprising administering to a subject an immunogenic composition comprising one or more *Plasmodium falciparum* or *Plasmodium vivax* pre-fertilization antigens, thereby blocking transmission of *Plasmodium falciparum* or *Plasmodium vivax* in the subject.

In another aspect, the invention features a method of immunizing a subject against *Plasmodium falciparum* or *Plasmodium vivax* comprising administering to a subject an immunogenic composition comprising one or more *Plasmodium falciparum* or *Plasmodium vivax* pre-fertilization antigens, thereby immunizing the subject against *Plasmodium falciparum* or *Plasmodium vivax.*

In still another aspect, the invention features a method for treating or preventing malaria in a subject comprising administering to a subject an immunogenic composition comprising one or more *Plasmodium falciparum* or *Plasmodium vivax* pre-fertilization antigens, thereby preventing malaria in the subject.

In another aspect, the invention features a method of blocking transmission of *Plasmodium falciparum* or *Plasmodium vivax* in a subject comprising administering to a subject an immunogenic composition comprising one or more *Plasmodium falciparum* or *Plasmodium vivax* post-fertilization antigens, thereby blocking transmission of *Plasmodium falciparum* or *Plasmodium vivax* in the subject.

In one aspect, the invention features a method of immunizing a subject against *Plasmodium falciparum* or *Plasmodium*

*vivax* comprising administering to a subject an immunogenic composition comprising one or more *Plasmodium falciparum* or *Plasmodium vivax* post-fertilization antigens, thereby immunizing the subject against *Plasmodium falciparum* or *Plasmodium vivax*.

In another aspect, the invention features a method for treating or preventing malaria in a subject comprising administering to a subject an immunogenic composition comprising one or more *Plasmodium falciparum* or *Plasmodium vivax* post-fertilization antigens, thereby preventing malaria in the subject.

In one embodiment of any one of the above aspects, the one or more pre-fertilization or post-fertilization antigens are selected from the group consisting of Pfs48/45, Pfs 230, Pfs25, Pvs48/45, Pvs 230 and Pvs25.

In a further embodiments, the pre-fertilization antigen is Pfs48/45.

In another further embodiment, the post-fertilization antigen is Pfs25.

In another embodiment of any one of the above aspects, the one or more pre-fertilization antigens or post-fertilization antigens is derived from a codon harmonized gene. In a particular embodiment, the codon harmonized gene is encoded by the amino acid sequence corresponding to SEQ ID NO: 1. In another particular embodiment, the codon harmonized gene is encoded by the amino acid sequence corresponding to SEQ ID NO: 3. In still another particular embodiment, the codon harmonized gene is encoded by the amino acid sequence corresponding to SEQ ID NO: 5.

In another aspect, the present invention features a method of blocking transmission of *Plasmodium falciparum* or *Plasmodium vivax* in a subject comprising administering to a subject an immunogenic composition comprising one or more *Plasmodium falciparum* or *Plasmodium vivax* surface antigens, thereby blocking transmission of *Plasmodium falciparum* or *Plasmodium vivax* in the subject.

In another preferred aspect, the invention features a method of immunizing a subject against *Plasmodium falciparum* or *Plasmodium vivax* comprising administering to a subject an immunogenic composition comprising one or more *Plasmodium falciparum* or *Plasmodium vivax* surface antigens, thereby immunizing the subject against *Plasmodium falciparum* or *Plasmodium vivax*.

In still another aspect, the invention features a method for treating or preventing malaria in a subject comprising administering to a subject an immunogenic composition comprising one or more *Plasmodium falciparum* or *Plasmodium vivax* surface antigens, thereby preventing malaria in the subject.

In one embodiment of any one of the above aspects, the surface antigens are gametocyte or gamete surface antigens.

In a related embodiment, the gametocyte or gamete surface antigens are selected from the group consisting of: Pfs48/45, Pfs230, Pvs48/45 and Pvs230.

In another further embodiment of any one of the above aspects, the surface antigens are midgut parasite surface antigens. In a related embodiment, the midgut parasite surface antigens are selected from the group consisting of: Pfs25, Pfs28, Pvs25 and Pvs28.

In still another further embodiment of any one of the above aspects, the one or more surface antigens is derived from a codon harmonized gene.

In another related embodiment, the codon harmonized gene is encoded by the amino acid sequence corresponding to SEQ ID NO: 1. In another embodiment, the codon harmonized gene is encoded by the amino acid sequence corresponding to SEQ ID NO: 3. In another further embodiments, the codon harmonized gene is encoded by the amino acid sequence corresponding to SEQ ID NO: 5.

In another further embodiment of any one of the above aspects, blocking transmission is measured by the reduction of mosquito oocysts by sera or plasma from a subject treated with the immunogenic composition compared to a control subject. In a further related embodiment, pre-immune sera from the treated subject and the control subject are used as a measure of 100% transmission for the corresponding test sera.

In another further embodiment of any one of the above aspects, the method further comprises administering an adjuvant. In a related embodiment, the adjuvant is selected from water-in-oil emulsion or Aluminum hydroxide.

In another further embodiment of any one of the above aspects, the method further comprises administering the immunogenic composition in one or more booster administrations. In a particular embodiment, the booster immunization is administered at 4 weeks. In another particular embodiment, the booster immunization is administered at 12 weeks.

In another further embodiment of any one of the above aspects, the method further comprises treatment with an additional agent. In a further embodiment, the additional agent is used to treat or prevent malaria.

In another further embodiment of any one of the above aspects, the composition is administered by one or more routes selected from the group consisting of: subcutaneous, intradermal, intramuscular, intravenous and transdermal delivery.

In still another further embodiment of any one of the above aspects, the composition is administered in a concentration between 1-100 μg.

In another aspect, the invention features an immunogenic composition comprising one or more pre-fertilization or post-fertilization antigens from *P. falciparium* or *P. vivax*.

In one embodiment, the one or more pre-fertilization or post-fertilization antigens are selected from the group consisting of Pfs48/45, Pfs230, Pfs 28, Pfs25, Pvs48/45, Pvs 230, Pvs 28, and Pvs25.

In a particular embodiment, the pre-fertilization antigen is Pfs48/45

In another particular embodiment, the post-fertilization antigen is Pfs25.

In still another further embodiment, the one or more pre-fertilization or post-fertilization antigens is derived from a codon harmonized gene.

In a further related embodiment, the codon harmonized gene encodes a protein represented by the amino acid sequence corresponding to SEQ ID NO: 1. In another embodiment, the codon harmonized gene is encoded by the amino acid sequence corresponding to SEQ ID NO: 3. In another further embodiment, the codon harmonized gene is encoded by the amino acid sequence corresponding to SEQ ID NO: 5.

In another further embodiment of any one of the above aspects, the composition is designed for expression in *E. coli*.

In another aspect, the invention features a vector comprising a codon harmonized Pfs48/45 sequence suitable for expression in a cell.

In still another aspect, the invention features a vector comprising a codon harmonized Pvs48/45 sequence suitable for expression in a cell.

In yet another aspect, the invention features a vector comprising a codon harmonized Pfs25 sequence suitable for expression in a cell.

In one embodiment, the codon harmonized Pfs48/45 sequence corresponds to the nucleic acid sequence comprising SEQ ID NO: 2. In another embodiment, the codon harmonized Pfs25 sequence corresponds to the nucleic acid sequence comprising SEQ ID NO: 4. In still another embodiment, the codon harmonized Pvs48/45 sequence corresponds to the nucleic acid sequence comprising SEQ ID NO: 6.

In one embodiment of any one of the above aspects, the invention features a cell expressing the vector of any one of the aspects described.

In one embodiment, the cell is an *E. coli* cell or an *E. coli* derivative cell.

In another aspect, the invention features a kit comprising an immunogenic composition comprising one or more *Plasmodium falciparum* or *Plasmodium vivax* pre-fertilization or post-fertilization antigens, and instructions for use in reducing transmission of *Plasmodium falciparum* or *Plasmodium vivax*.

In yet another aspect, the invention features a kit comprising an immunogenic composition comprising one or more *Plasmodium falciparum* or *Plasmodium vivax* pre-fertilization or post-fertilization antigens, and instructions for use in preventing malaria.

In one embodiment, the one or more pre-fertilization or post-fertilization antigens are selected from the group consisting of Pfs48/45, Pfs230, Pfs 28, Pfs25, Pvs48/45, Pvs 230, Pvs 28, and Pvs25.

In another particular embodiment, the one or more pre-fertilization or post-fertilization antigens is derived from a codon harmonized gene.

In another aspect, the invention features a method for preparing a codon harmonized pre-fertilization or post-fertilization antigen sequence encoded by a *P. falciparum* or *P. vivax* pre-fertilization or post-fertilization gene comprising determining the frequency of codon usage of the pre-fertilization or post-fertilization gene coding sequence; and substituting codons in the coding sequence with codons of similar frequency from a host cell which code for the same pre-fertilization or post-fertilization antigen, thereby preparing a codon harmonized pre-fertilization or post-fertilization antigen sequence.

In one embodiment, the one or more pre-fertilization or post-fertilization genes are selected from the group consisting of Pfs48/45, Pfs230, Pfs 28, Pfs25, Pvs48/45, Pvs 230, Pvs 28, and Pvs25.

In another aspect, the invention features a method for preparing a codon harmonized Pfs48/45 antigen sequence encoded by a pre-fertilization or post-fertilization gene comprising determining the frequency of codon usage of the pre-fertilization or post-fertilization gene coding sequence, wherein the Pfs48/45 sequence corresponding to the nucleic acid sequence represented by SEQ ID NO: 7, and substituting codons in the coding sequence of SEQ ID NO: 7 with codons of similar frequency from a host cell which code for the Pfs48/45 antigen, thereby preparing a codon harmonized Pfs48/45 antigen sequence.

In one embodiment, the codon harmonized gene is expressed in a host cell.

In another embodiment, the host cell is *E. coli* or an *E. coli* derivative.

In still another embodiment, the invention features a codon harmonized nucleotide sequence prepared according to the methods described herein.

Other features and advantages of the invention will be apparent from the detailed description, and from the claims.

BRIEF DESCRIPTION OF THE DRAWINGS

The following Detailed Description, given by way of example, but not intended to limit the invention to specific embodiments described, may be understood in conjunction with the accompanying drawings, incorporated herein by reference.

Various preferred features and embodiments of the present invention will now be described by way of non-limiting example and with reference to the accompanying drawings in which.

DETAILED DESCRIPTION OF THE INVENTION

Definitions

Figure 1D:
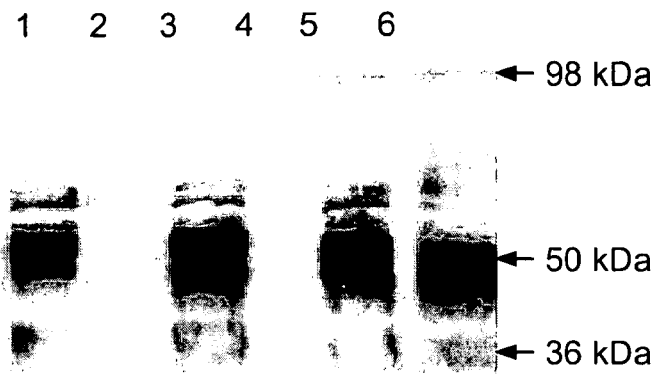
FIG. 1 (*a-f*) shows the purification and characterization of CH-rPfs48/45. (a) Schematic representation of amino acid residues in the recombinant protein expressed. First 16 amino residues at the N-terminus contain 6× Histidine residues and a short linker to allow affinity purification of the protein. The sequence of Pfs48/45 begins with asparagine (N) at the 28 position and ends with serine (S) at 427 position in the native Pfs48/45 sequence. (b) Induction profile of CH-rPfs48/45. The cells were induced with 0.1 mM IPTG for 3 h and lysed by sonication. Lysates of uninduced and induced cells either non-reduced (left panel), or reduced (treated with 10 mM 2-mercaptoethanol, right panel) were run on SDS-polyacrylamide gel and stained with Coomassie stain. Lane 1; Protein molecular weight marker; lane 2, uninduced cell lysate; lane 3, induced cell lysate. The induced protein band in both non-reduced and reduced gels are encircled for easy recognition. (c) Flow diagram of various major steps including differential detergent extractions used for protein purification. (d) Western blot analysis for the presence of CH-rPfs48/45 at each step of detergent extraction using anti-His mAb. Lane 1, lysate pellet; lane 2, lysate supernatant; lane 3, 1% Tween-80 pellet; lane 4, 1% Tween-80 supernatant; lane 5, 0.5% sarcosyl pellet; lane 6, 0.5% sarcosyl supernatant. (e) Western blot analysis of purified CH-rPfs48/45 using anti-His mAb. Lane 1, eluate from Ni-NTA column; lane 2, dialyzed CH-rPfs48/45. (f) Recognition of CH-rPfs48/45 by conformation specific mAb IIC5B10. Lane 1, non-reduced CH-rPfs48/45; lane 2, reduced CH-rPfs48/45.
Figure 1E:
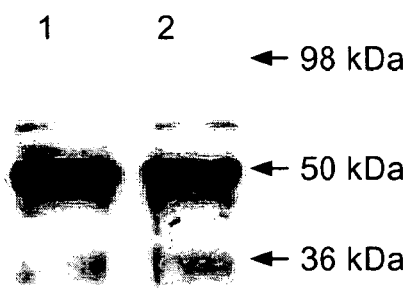

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, for example, hydroxyproline, gamma-carboxyglutamate, and O-phosphoserine, phosphothreonine.

The term "codon harmonization" is meant to refer to a process that harmonizes codon usage frequency of a target gene with those of the expression host for heterologous expression of protein. In preferred embodiments, codon harmonization refers to an algorithm where synonymous codons from E. coli are selected that closely resemble the codon usage of a native pre-implantation gene, for example the Pfs48/45 gene, including regions coding 'link/end' segments of proteins in P. falciparum.

By "fragment" is meant a portion (e.g., at least 10, 25, 50, 100, 125, 150, 200, 250, 300, 350, 400, or 500 amino acids or nucleic acids) of a protein or nucleic acid molecule that is substantially identical to a reference protein or nucleic acid and retains the biological activity of the reference. In some embodiments the portion retains at least 50%, 75%, or 80%, or more preferably 90%, 95%, or even 99% of the biological activity of the reference protein or nucleic acid described herein.

The term "host cell" is meant to refer to a cell into which a foreign gene is introduced. The host cell can be prokaryotic or eukaryotic. In preferred embodiments, the host cell is E. coli or an E. coli derivative.

By "immunogenic composition" is meant to refer to one or more Plasmodium pre-fertilization or post-fertilization antigens that is capable of eliciting protection against malaria, whether partial or complete. An immunogenic composition may also be useful for treatment of an infected individual.

The terms "isolated," "purified," or "biologically pure" refer to material that is free to varying degrees from components which normally accompany it as found in its native state. Various levels of purity may be applied as needed according to this invention in the different methodologies set forth herein; the customary purity standards known in the art may be used if no standard is otherwise specified.

By "isolated nucleic acid molecule" is meant a nucleic acid (e.g., a DNA, RNA, or analog thereof) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule which is transcribed from a DNA molecule, as well as a recombinant DNA which is part of a hybrid gene encoding additional polypeptide sequence.

By "nucleic acid" is meant an oligomer or polymer of ribonucleic acid or deoxyribonucleic acid, or analog thereof. This term includes oligomers consisting of naturally occurring bases, sugars, and intersugar (backbone) linkages as well as oligomers having non-naturally occurring portions which function similarly. Such modified or substituted oligonucleotides are often preferred over native forms because of properties such as, for example, enhanced stability in the presence of nucleases.

The term "complimentary nucleic acid sequences" refer to contiguous DNA or RNA sequences which have compatible nucleotides (e.g., A/T, G/C) in corresponding positions, such that base pairing between the sequences occurs. For example, the sense and anti-sense strands of a double-stranded DNA helix are known in the art to be complimentary.

By "pre- or post-fertilization antigen" is meant to refer to a protein target expressed in Plasmodium that is necessary for Plasmodium transmission in a host. In particular embodiments, prefertilization antigens refer to antigens expressed in the intraerythrocytic gamtocytes and male and female gametes prior to fertilization process. Examples include, but are not limited to, proteins such as Pfs230 and Pfs48/45 in P. falciparum or Pvs230 and Pvs48/45 in P. vivax. In other particular embodiments, post fertilization antigens refer to antigens expressed on the surface of zygotes formed after fertilization between female and male gametes and ookinetes. Examples include, but are not limited to, proteins such as Pfs25 and Pfs28 in P. falciparum and Pvs25 and Pvs28 in P. vivax.

By "protein" is meant any chain of amino acids, or analogs thereof, regardless of length or post-translational modification.

By "reference" is meant a standard or control condition.

By "specifically binds" is meant a molecule (e.g., peptide, polynucleotide) that recognizes and binds a protein or nucleic acid molecule of the invention, but which does not substantially recognize and bind other molecules in a sample, for example, a biological sample, which naturally includes a protein of the invention.

As used herein, the terms "treat," "treating," "treatment," and the like refer to reducing or ameliorating a disorder and/or symptoms associated therewith, for example malaria. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition, for example malaria.

Other definitions appear in context throughout the disclosure.

Compositions

The present invention features immunogenic compositions comprising one or more pre-fertilization or post-fertilization antigens from *Plasmodium*, preferably *P. falciparum* or *P. vivax*. The genome of *Plasmodium falciparum* has been completely sequenced. (Gardner et al., Nature, 419:498-511 (2002)).

Preferably, the one or more of pre-fertilization or post-fertilization antigens are selected from the group consisting of Pfs48/45, Pfs230, Pfs 28, Pfs25, Pvs48/45, Pvs 230 Pvs 28, and Pvs25. Most preferably, the antigen is Pfs 48/45 or Pfs25 of *P. falciparum*. Alternatively, the antigen is Pvs 48/45 or Pvs25 of *P. vivax*.

Pfs230 and Pfs48/45 can be classified as gametocyte and gamete (male and female) surface antigens. Pfs25 and Pfs28 can be classified as mosquito midgut parasite stages (zygote and ookinete) surface antigens.

Targeted gene disruption studies have shown that Pfs48/45 plays a critical role in male gamete fertility, an important aspect of the sexual reproduction success of the parasite [14]. Analysis of immune human sera in endemic areas has also suggested a strong correlation between naturally present anti-Pfs48/45 antibodies and transmission reducing activity of those human sera; thus making it a key candidate for vaccine development [15]. However, efforts to produce full length recombinant Pfs48/45 in a functional conformation have largely remained unsuccessful. In a recent study, an approach that involved co-expression of a truncated version of C-terminal fragment of Pfs48/45 fused with a large fusion partner maltose binding protein (MBP) along with four periplasmic folding catalysts DsbA, DsbC, FkpA and SurA resulted in correctly folded truncated product which produced high titers of transmission-reducing antibodies in immunized BALB/c mice [16]. In this recombinant expression approach periplasmic targeting and folding into functional conformation of expressed Pfs48/45 protein was strictly dependent upon fusion with MBP as a carrier protein and protein folding was catalyzed by four chaperons co-expressed in the host, respectively.

Pfs25 is a *P. falciparum* antigen expressed on the surface of the malaria parasite. Pfs25 consists of four epidermal growth factor (EGF)-like domains located between a secretory signal sequence at the N-terminus, and a short C-terminal hydrophobic domain, which seems involved in the transfer of the EGF-like domains to a glycosyl-phosphatidylinositol (GPI) lipid anchor. There are 22 cysteine residues present as disulfide bonds in the four EGF-like domains of Pfs25. (Kaslow, et al., Trends in Biotechnology, 10:388-391 (1992); Kaslow, et al., Nature, 333:74-76 (1988)). The disulfide bonds between the cysteine residues are essential for maintaining the structural integrity of the antigen. In an ex vivo experiment, antibodies to the antigen can completely block transmission of *P. falciparum*. (Vermeulen, et al., J. Exp. Med. 162:1460-1476 (1985)) The counterpart of Pfs25 in *P. vivax* is Pvs25.

It is a novel feature of the present invention that the one or more pre-fertilization or post-fertilization antigens is derived from a codon harmonized gene.

Codon Harmonization

It has been discovered that a nucleotide sequence capable of enhanced expression in host cells can be obtained by harmonizing the frequency of codon usage in the foreign gene at each codon in the coding sequence to that used by the host cell.

In certain embodiments, the invention features a nucleic acid sequence encoding a polypeptide to enhance expression and accumulation of the polypeptide in the host cell. Accordingly, the present invention provides novel nucleic acid sequences, encoding a polypeptide or protein that is foreign to a host cell, and that is expressed at greater levels and with greater biological activity than in the host cell as compared to the wild-type sequence if expressed in the same host cell.

Certain examples of codon harmonization have been described, for example, in US Application Nos. 20060088547 and 20080076161 and Angov et al. (PLOS, 2008. Volume 3, issue 5), which are incorporated by reference in their entireties herein.

The methods of the present invention, while directed to codon harmonization of pre- or post-fertilization antigens, are not limited as such, and are applicable to any coding sequence encoding a protein foreign to a host cell in which the protein is expressed.

Accordingly, in certain embodiments the invention features a method for preparing a codon harmonized pre-fertilization or post-fertilization antigen sequence encoded by *P. falciparum* or *P. vivax* a pre-fertilization or post-fertilization gene comprising determining the frequency of codon usage of the pre-fertilization or post-fertilization gene coding sequence, and substituting codons in the coding sequence with codons of similar frequency from a host cell which code for the same pre-fertilization or post-fertilization antigen, thereby preparing a codon harmonized pre-fertilization or post-fertilization antigen sequence.

For example, the frequency of occurrence of each codon in the *P. falciparum* or *P. vivax* pre-fertilization or post-fertilization gene of interest can be calculated and replaced with an *E. coli* codon with a similar frequency for the same amino acid. Preferably, the one or more pre-fertilization or post-fertilization genes are selected from the group consisting of Pfs48/45, Pfs230, Pfs 28, Pfs25, Pvs48/45, Pvs 230, Pvs 28, and Pvs25.

An existing DNA sequence can be used as the starting material and modified by standard mutagenesis methods that are known to those skilled in the art or a synthetic DNA sequence having the desired codons can be produced by known oligonucleotide synthesis, PCR amplification, and DNA ligation methods.

For example, the invention features a method for preparing a codon harmonized Pfs48/45 antigen sequence encoded by a pre-fertilization or post-fertilization gene comprising determining the frequency of codon usage of the pre-fertilization or post-fertilization gene coding sequence, wherein the Pfs48/45 sequence corresponding to the nucleic acid sequence represented by SEQ ID NO: 7, and substituting codons in the coding sequence of SEQ ID NO: 7 with codons of similar frequency from a host cell which code for the Pfs48/45 antigen, thereby preparing a codon harmonized Pfs48/45 antigen sequence.

The native sequence of Pfs48/45 is represented by NCBI accession number AF356146, corresponding to SEQ ID NO: 7 shown below:

```
                                                     SEQ ID NO: 7
   1 atgatgttat atatttctgc gaaaaaggct caagttgctt tcatcttata tatagtattg 61 gtattaagaa taataagtgg aaacaatgat ttttataatc ctagcgcttt gaatagtgaa 121 atatctggat ttataggata taagtgtaat ttttcaaatg aaggtgttca taatttaaag 181 ccagatatgc gtgaacgtag gtctattttt tgcaacatcc attcgtattt tatatatgat 241 aagataagat taataatacc taaaaaaagt tcgtcacctg agtttaaaat attacccgaa 301 aaatgttttc aaaaagtata tactgattat gagaatagag ttgaaactga tatatcggaa 361 ttaggtttaa ttgaatatga aatagaagaa aatgatacaa accctaatta taatgaaagg 421 acaataacta tatctccatt tagtccaaaa gacattgaat ttttttgttt ttgtgataat 481 actgaaaagg ttatatcaag tatagaaggg agaagtgcta tggtacatgt acgtgtatta 541 aaatatccac ataatatttt atttactaat ttaacaaatg atcttttttac atatttgccg 601 aaaacatata atgaatctaa ttttgtaagt aatgtattag aagtagaatt aaatgatgga 661 gaattatttg ttttagcttg tgaactaatt aataaaaaat gttttcaaga aggaaaagaa 721 aaagccttat ataaaagtaa taaaataatt tatcataata agttaactat ctttaaagct 781 ccattttatg ttcatcaaa agatgttaat acagaatgta catgcaaatt taaaaataat 841 aattataaaa tagttttaaa accaaaatat gaaaaaaaag tcatacacgg atgtaacttc 901 tcttcaaatg ttagttctaa acatactttt acagatagtt tagatatttc tttagttgat 961 gatagtgcac atatttcatg taacgtacat ttgtctgaac caaatataa tcatttggta 1021 ggtttaaatt gtcctggtga tattatacca gattgctttt ttcaagtata tcaacctgaa 1081 tcagaagaac ttgaaccatc caacattgtt tatttagatt cacaaataaa tataggagat 1141 attgaatatt atgaagatgc tgaaggagat gataaaatta aattatttgg tatagttgga 1201 agtataccaa aaacgacatc ttttacttgt atatgtaaga aggataaaaa aagtgcttat 1261 atgacagtta ctatagattc agcatattat ggattttttgg ctaaaacatt tatattccta 1321 attgtagcaa tattattata tatttag
```

DNA sequences modified by the method of the present invention are expressed at a greater level in host cells than the corresponding non-modified DNA sequence. Preferably, the host cell is *E. coli* or an *E. coli* derivative. The method can be applied to any DNA sequence for introduction into a host cell to provide protein product.

In particular exemplary embodiments of the present invention, the codon harmonized gene corresponds to the amino acid sequence corresponding to SEQ ID NO: 1, shown below, and the corresponding nucleic acid sequence, SEQ ID NO: 2.

```
                                                     SEQ ID NO: 1
NNDFYNPSALNSEISGFIGYKCNFSNEGVHNLKPDMRERRSIFCNIH

SYFIYDKIRLIIPKKSSSPEFKILPEKCFQKVYTDYENRVETDISEL

GLIEYEIEENDTNPNYNERTITISPFSPKDIEFFCFCDNTEKVISSI

EGRSAMVHVRVLKYPHNILFTNLTNDLFTYLPKTYNESNFVSNVLEV

ELNDGELFVLACELINKKCFQEGKEKALYKSNKIIYHNKLTIFKAPF
```

```
YVTSKDVNTECTCKFKNNNYKIVLKPKYEKKVIHGCNFSSNVSSKHT

FTDSLDISLVDDSAHISCNVHLSEPKYNHLVGLNCPGDIIPDCFFQV

YQPESEELEPSNIVYLDSQINIGDIEYYEDAEGDDKIKLFGIVGSIP

KTTSFTCICKKDKKSAYMTVTIDS
```

```
                                                     SEQ ID NO: 2
AATAACGACTTCTACAACCCATCGGCTCTCAACTCTGAAATCAGCGG

CTTCATCGGCTACAAGTGCAACTTCAGCAACGAAGGCGTTCACAACC

TGAAGCCAGACATGCGAGAACGACGCAGCATTTTCTGTAATATACAC

TCGTACTTCATCTACGACAAGATCCGTCTGATCATCCCAAAAAAAAG

CTCGAGCCCAGAGTTCAAAATCCTGCCTGAAAAATGCTTCCAGAAAG

TTTACACTGACTACGAGAACCGTGTTGAAACTGACATCTCGGAACTG

GGCCTGATTGAATACGAAATCGAAGAAAACGACACCAATCCAAACTA

CAACGAACGCACCATCACGATCAGCCCATTCTCTCCAAAAGATATTG

AATTCTTCTGCTTCTGCGACAACACTGAAAAGGTTATCAGCTCTATC
```

-continued
GAAGGGCGTTCTGCTATGGTTCACGTACGAGTTCTGAAATACCCACA

CAACATTCTGTTCACTAACCTGACCAACGACCTCTTCACCTACCTCC

CTAAAACCTACAACGAAAGCAACTTCGTTTCTAACGTTCTGGAAGTT

GAACTGAACGACGGCGAACTGTTCGTTCTGGCTTGCGAACTCATTAA

CAAAAAATGCTTCCAGGAAGGCAAAGAAAAAGCCCTGTACAAATCTA

ACAAAATCATTTACCACAACAAGCTCACTATATTCAAAGCTCCATTC

TACGTTACCAGCAAAGACGTTAACACCGAATGCACCTGTAAATTCAA

AAACAACAACTACAAAATCGTTCTGAAACCAAAATACGAAAAAAAG

TCATCCATGGCTGCAATTTTAGCAGCAACGTATCTAGCAAACACACT

TTCACCGACTCTCTGGACATTAGCCTGGTTGACGACTCTGCTCACAT

TAGCTGCAATGTTCACCTCAGCGAACCAAAATACAACCACCTCGTTG

GCCTGAACTGCCCAGGCGACATTATCCCAGACTGTTTCTTCCAGGTT

TACCAGCCAGAAAGCGAAGAACTCGAACCATCGAATATTGTTTACCT

GGACAGCCAGATCAACATCGGCGACATTGAATACTACGAAGACGCTG

AAGGCGACGACAAAATTAAACTGTTCGGCATCGTTGGCTCTATCCCA

AAAACGACCAGCTTCACTTGCATCTGCAAGAAGGACAAAAAATCTGC

TTACATGACCGTTACTATCGACTCT

SEQ ID NO: 2 preferably includes a signal and anchor sequence.

SEQ ID NO: 9 corresponds to the codon harmonized DNA sequence (SEQ ID NO:2, shown in italics) and restriction enzyme sites shown in bold, 6× histidine codons shown as underlined, as affinity tags, and linker sequences, preferably used to facilitate cloning.

SEQ ID NO: 9
CATATGGCA<u>CACCATCATCATCATCAT</u>CCCGGGGGATCCGGTTCTGG

*TACCAATAACGACTTCTACAACCCATCGGCTCTCAACTCTGAAATCA*

*GCGGCTTCATCGGCTACAAGTGCAACTTCAGCAACGAAGGCGTTCAC*

*AACCTGAAGCCAGACATGCGAGAACGACGCAGCATTTTCTGTAATAT*

*ACACTCGTACTTCATCTACGACAAGATCCGTCTGATCATCCCAAAAA*

*AAAGCTCGAGCCCAGAGTTCAAAATCCTGCCTGAAAAATGCTTCCAG*

*AAAGTTTACACTGACTACGAGAACCGTGTTGAAACTGACATCTCGGA*

*ACTGGGCCTGATTGAATACGAAATCGAAGAAAACGACACCAATCCAA*

*ACTACAACGAACGCACCATCACGATCAGCCCATTCTCTCCAAAAGAT*

*ATTGAATTCTTCTGCTTCTGCGACAACACTGAAAAGGTTATCAGCTC*

*TATCGAAGGGCGTTCTGCTATGGTTCACGTACGAGTTCTGAAATACC*

*CACACAACATTCTGTTCACTAACCTGACCAACGACCTCTTCACCTAC*

*CTCCCTAAAACCTACAACGAAAGCAACTTCGTTTCTAACGTTCTGGA*

*AGTTGAACTGAACGACGGCGAACTGTTCGTTCTGGCTTGCGAACTCA*

*TTAACAAAAAATGCTTCCAGGAAGGCAAAGAAAAAGCCCTGTACAAA*

*TCTAACAAAATCATTTACCACAACAAGCTCACTATATTCAAAGCTCC*

*ATTCTACGTTACCAGCAAAGACGTTAACACCGAATGCACCTGTAAAT*

-continued
*TCAAAAACAACAACTACAAAATCGTTCTGAAACCAAAATACGAAAAA*

*AAAGTCATCCATGGCTGCAATTTTAGCAGCAACGTATCTAGCAAACA*

*CACTTTCACCGACTCTCTGGACATTAGCCTGGTTGACGACTCTGCTC*

*ACATTAGCTGCAATGTTCACCTCAGCGAACCAAAATACAACCACCTC*

*GTTGGCCTGAACTGCCCAGGCGACATTATCCCAGACTGTTTCTTCCA*

*GGTTTACCAGCCAGAAAGCGAAGAACTCGAACCATCGAATATTGTTT*

*ACCTGGACAGCCAGATCAACATCGGCGACATTGAATACTACGAAGAC*

*GCTGAAGGCGACGACAAAATTAAACTGTTCGGCATCGTTGGCTCTAT*

*CCCAAAAACGACCAGCTTCACTTGCATCTGCAAGAAGGACAAAAAAT*

*CTGCTTACATGACCGTTACTATCGACTCT*TGATAAGCGGCCGC

In other embodiments of the invention, the codon harmonized gene corresponds to the amino acid sequence corresponding to SEQ ID NO: 3, shown below, and the corresponding nucleic acid sequence, SEQ ID NO: 4.

SEQ ID NO: 3
KYNNAKVTVDTVCKRGFLIQMSGHLECKCENDLVINNEETCEEKVLKC

DEKTVNKPCGDFSKCIKIDGNPVSYACKCNLGYDMVNNVCIPNECKNV

TCGNGKCILDTSNPVKTGVCSCNIGKVPNVQDQNKCSKDGETKCSLKC

LKENETCKAVDGIYKCDCKDGFIIDNESSICTAFSAYNILN

SEQ ID NO: 4
AAGTATAACAACGCCAAAGTTACTGTCGACACTGTATGTAAACGTGGT

TTCCTGATTCAAATGAGCGGCCACCTCGAATGCAAATGCGAAAACGAC

CTGGTCCTGGTAAACGAAGAAACCTGCGAAGAAAAAGTTTTAAAATGC

GATGAAAAGACTGTAAACAAACCGTGCGGTGACTTCTCGAAATGCATT

AAAATTGACGGTAACCCTGTTTCTTATGCTTGCAAATGCAACCTCGGT

TACGACATGGTAAACAACGTTTGCATTCCGAACGAATGCAAGAACGTA

ACTTGCGGCAATGGCAAATGCATTCTGGACACCTCGAACCCAGTTAAA

ACTGGTGTTTGTTCTTGCAACATTGGGAAAGTTCCTAACGTACAGGAC

CAGAACAAATGCTCTAAAGACGGTGAAACGAAATGTTCTCTGAAATGT

CTGAAAGAAAACGAAACGTGCAAAGCTGTTGACGGTATTTACAAATGC

GACTGCAAAGACGGTTTCATTATTGACAACGAATCGAGCATTTGCACT

GCTTTCTCTGCTTACAACATTCTGAAC

SEQ ID NO:4 preferably includes a signal and anchor sequence.

SEQ ID NO: 8 corresponds to the codon harmonized DNA sequence (SEQ ID NO:4, shown in italics) and restriction enzyme sites shown in bold, 6× histidine codons shown as underlined, as affinity tags, and linker sequences, preferably used to facilitate cloning.

SEQ ID NO: 8
CATATGG<u>CACACCATCATCATCATCAT</u>CCCGGGGGATCCGGTTCTGGT

*ACCAAGTATAACAACGCCAAAGTTACTGTCGACACTGTATGTAAACGT*

*GGTTTCCTGATTCAAATGAGCGGCCACCTCGAATGCAAATGCGAAAAC*

*GACCTGGTCCTGGTAAACGAAGAAACCTGCGAAGAAAAAGTTTTAAAA*

-continued

```
TGCGATGAAAAGACTGTAAACAAACCGTGCGGTGACTTCTCGAAATGC

ATTAAAATTGACGGTAACCCTGTTTCTTATGCTTGCAAATGCAACCTC

GGTTACGACATGGTAAACAACGTTTGCATTCCGAACGAATGCAAGAAC

GTAACTTGCGGCAATGGCAAATGCATTCTGGACACCTCGAACCCAGTT

AAAACTGGTGTTTGTTCTTGCAACATTGGGAAAGTTCCTAACGTACAG

GACCAGAACAAATGCTCTAAAGACGGTGAAACGAAATGTTCTCTGAAA

TGTCTGAAAGAAAACGAAACGTGCAAAGCTGTTGACGGTATTTACAAA

TGCGACTGCAAAGACGGTTTCATTATTGACAACGAATCGAGCATTTGC

ACTGCTTTCTCTGCTTACAACATTCTGAACTGATAAGCGGCCGC
```

In other exemplary embodiments of the present invention, the codon harmonized gene corresponds to the amino acid sequence corresponding to SEQ ID NO: 5, shown below, and the corresponding nucleic acid sequence, SEQ ID NO: 6. SEQ ID NO: 5 shows the full length peptide sequence, where the signal peptide and the GPI anchor position are in bold.

MLKRQLANLLLVLSLLRGITHTQMAKGEVKYVPPEELNKDVSGFFGFK

CNFSSKGVHNLEPILTEKRSLVCSIYSYFIYDKIKLTIPKKIPGSKFK

MLPEKCFQTVYTNYEKRTEEKIENMGLVEYEVKEDDSNSEYTEKILTI

SPFNTKDVEFFCICDNSENVISNVKGRVALVQVNVLKYPHKITSINLT

KEPYSYLPNQVDKTSFKSHKLDLELQDGELVVLACEKVDDKCFKKGKD

TSPLSLYKSKKIVYHKNLSIFKAPVYVKSADVTAECSCNVDSTIYTLS

LKPVYTKKLIHGCNFSSDKSTHNFTNHVDMAELGENAQITCSIELVDT

SYNHLIGMSCPGEVLPECFFQVYQRESPELEPSKIVYLDAQLNIGNVE

YFEDSKGENIVKIFGLVGSIPKTTSFTCICRKGKKIGYMSVK**IAAGYF

GFLAKIFILLIVLLLLYF***

SEQ ID NO:6 corresponds to the codon harmonized Pvs48/45 DNA sequence consisting of 1274 bases, not including the signal sequence and minus GPI anchor sequence shown in SEQ ID NO:5.

```
                                    SEQ ID NO: 6
CATATGGCACACCATCATCATCATCATCCCGGGGGATCCGGTTCTGGT

ACCATGGCCAAGGGCGAGGTCAAATATGTGCCTCCAGAGGAGCTGAAT

AAGGATGTGAGCGGCTTTTTTGGGTTTAAGTGTAATTTTAGCAGCAAG

GGCGTCCATAACCTCGAGCCTATTCTGACGGAGAAGCGAAGCCTGGTC

TGTAGCATTTATAGCTATTTTATTTATGATAAGATTAAACTGACGATT

CCTAAAAAAATTCCAGGCTCGAAGTTTAAGATGCTCCCAGAGAAGTGT

TTTCAAACGGTGTATACTAATTATGAGAAGCGCACGGAGGAGAAGATT

GAGAATATGGGCCTCGTGGAGTATGAGGTGAAGGAGGATGATAGCAAC

TCGGAGTATACGGAAGATTCTGACGATTAGCCCTTTTAACACGAAA

GATGTGGAGTTTTTTTGTATTTGTGATAACTCGGAGAACGTCATTAGC

AATGTGAAAGGCCGAGTGGCGCTCGTGCAAGTGAATGTGCTCAAGTAT

CCTCATAAGATTACGAGCATTAACCTGACGAAAGAGCCATATTCGTAT
```

```
CTGCCTAATCAAGTGGATAAAACGAGCTTTAAGTCGCATAAGCTCGAT

CTCGAGCTCCAAGATGGCGAGCTCGTGGTGCTCGCGTGTGAGAAGGTG

GATGATAAGTGTTTTAAGAAAGGCAAAGATACTAGCCCACTGAGCCTC

TATAAAAGCAAGAAGATTGTGTATCATAAAAACCTCAGCATTTTTAAG

GCGCCTGTGTATGTGAAGAGCGCCGATGTGACGGCGGAGTGTAGCTGT

AATGTGGATAGCACGATTTATACTCTCAGCCTCAAGCCTGTGTATACG

AAGAAACTCATTCATGGGTGTAATTTTAGCTCGGATAAGAGCACGCAT

AATTTTACTAATCATGTGGATATGGCCGAGCTGGGGGAGAATGCGCAA

ATTACGTGTAGCATTGAGCTCGTGGATACGAGCTATAATCATCTCATT

GGCATGAGCTGTCCTGGGGAGGTGCTGCCTGAGTGTTTTTTTCAAGTG

TATCAACGAGAGAGCCCAGAGCTCGAGCCTAGCAAGATTGTCTATCTC

GATGCCCAACTCAATATTGGCAATGTGGAGTATTTTGAGGATAGCAAA

GGCGAGAATATTGTGAAGATTTTTGGGCTCGTGGGCAGCATTCCTAAG

ACGACGAGCTTTACGTGTATTTGTCGAAAAGGGAAAAAGATTGGGTAT

ATGAGCGTGAAGTGATAAGCGGCCGC
```

In still other embodiments of the present invention, the codon harmonized gene corresponds to the nucleic acid sequence shown as SEQ ID NO: 10, where SEQ ID NO: 10 is a codon harmonized Pfs230 C-terminal modified.

```
                                    SEQ ID NO: 10
CATATGGCACACCATCATCATCATCATCCCGGGGGATCCGGTTCTGGT

ACCAAAGAATATGTTTGCGCTTCACCGACCAGCTGAAACCGACCGAAT

CTGGCCCAAAAGTTAAAAAATGCGAAGTTAAAGTTAACGAGCCGCTGA

TCAAAGTTAAAATCATCTGCCCGCTGAAAGGCAGCGTTGAAAAACTGT

ACGACAACATCGAATACGTTCCAAAAAAATCGCCGTACGTTGTTCTGA

CCAAAGAGGAAACTAAACTCAAGGAAAAACTGTTGTCGAAACTCATTT

ACGGCCTGCTGATCAGCCCTACGGTTAATGAAAGGAGAACAACTTCA

AAGAAGGCGTTATTGAATTCACTCTGCCTCCAGTGGTTCATAAGGCTA

CCGTGTTCTACTTCATCTGCGACAACAGCAAAACCGAAGACGACAATA

AAAAAGGCAACCGTGGGATTGTTGAAGTGTACGTTGAACCGTACGGCA

ACAAAATTAACGGCTGCGCTTTTCTCGACGAAGACGAAGAAGAAGAAA

AATACGGCAACCAGATTGAAGAAGACGAACACAACGAGAAGATCAAAA

TGAAAACCTTTTTCACGCAAAACATCTACAAAAAAAACAACATCTACC

CGTGCTACATGAAACTGTACTCGGGCGACATCGGCGGCATTCTCTTCC

CAAAGAACATCAAAAGCACCACGTGCTTCGAAGAGATGATCCCATACA

ACAAAGAAATCAAATGGAACAAAGAAAACAAATCTCTGGGCAATCTGG

TTAACAACAGCGTTGTTTACAACAAAGAGATGAACGCTAAATACTTCA

ACGTTCAATACGTTCATATTCCAACCTCTTACAAAGACACCCTGAACC

TGTTCTGCTCTATTATCCTGAAAGAAGAGGAATCTAACCTGATTAGCA

CTAGCTACCTGGTTTACGTTTCTATTAACGAAGAACTGAACTTCAGCC

TCTTTGACTTCTACGAAAGCTTCGTTCCAATCAAAAAAAACGATCCAGG
```

```
TTGCTCAGAAGAACGTTAACAACAAAGAACACGACTACACCTGCGACT

TCACGGACAAACTGGACAAAACGGTTCCAAGCACTGCTAACGGGAAGA

AACTGTTCATCTGCCGTAAGCACCTGAAAGAATTCGACACCTTCACGC

TGAAATGCAACGTTAACAAAACCCAGTACCCGAACATAGAGATCTTCC

CAAAAACCCTGAAAGACAAAAAGGAAGTTCTGAAACTGGACCTCGACA

TCCAGTACCAGATGTTCTCTAAATTCTTCAAATTTAACACCCAAAACG

CTAAGTACCTGAACCTGTACCCGTACTACCTGATTTTCCCGTTCAACC

ACATCGGCAAAAAGAACTGAAAAACAACCCAACCTACAAAAACCACA

AAGACGTGAAATACTTCGAGCAGAGCAGCGTTCTGAGCCCTCTGAGCT

CGGCTGATTCTCTGGGGAAACTGCTGAACTTCCTGGACACTCAGGAGA

CGGTTTGCCTCACGGAAAAGATCCGTTACCTGAACCTGTCTATAAACG

AGCTGGGCAGCGACAACAACACCTTCAGCGTTACCTTCCAAGTTCCGC

CGTACATCGACATTAAGGAACCATTCTACTTCATGTTCGGCTGCAACA

ACAACAAAGGCGAAGGGAACATAGGCATTGTTGAACTGCTGATCAGCA

AGCAGTGATAAGCGGCCGC
```

Here, the bold, underlined sequence refers to restriction enzyme sites to facilitate cloning into an expression plasmid vector.

In other embodiments of the present invention, the codon harmonized gene corresponds to the nucleic acid sequence shown as SEQ ID NO: 11, where SEQ ID NO: 11 corresponds to codon harmonized Pf230 A2B3.

```
                                          SEQ ID NO: 11
CATATGGCACACCATCATCATCATCATCCCGGGGATCCGGTTCTGGT

ACCCACGACTACACCTGCGACTTCACGGACAAACTGGACAAAACGGTT

CCAAGCACTGCTAACGGGAAGAAACTGTTCATCTGCCGTAAGCACCTG

AAAGAATTCGACACCTTCACGCTGAAATGCAACGTTAACAAAACCCAG

TACCCGAACATAGAGATCTTCCCAAAAACCCTGAAAGACAAAAAGGAA

GTTCTGAAACTGGACCTCGACATCCAGTACCAGATGTTCTCTAAATTC

TTCAAATTTAACACCCAAAACGCTAAGTACCTGAACCTGTACCCGTAC

TACCTGATTTTCCCGTTCAACCACATCGGCAAAAAGAACTGAAAAAC

AACCCAACCTACAAAAACCACAAAGACGTGAAATACTTCGAGCAGAGC

AGCGTTCTGAGCCCTCTGAGCTCGGCTGATTCTCTGGGGAAACTGCTG

AACTTCCTGGACACTCAGGAGACGGTTTGCCTGACGGAAAAGATCCGT

TACCTGAACCTGTCTATAAACGAGCTGGGCAGCGACAACAACACCTTC

AGCGTTACCTTCCAAGTTCCGCCGTACATCGACATTAAGGAACCATTC

TACTTCATGTTCGGCTGCAACAACAACAAAGGCGAAGGGAACATAGGC

ATTGTTGAACTGCTGATCAGCAAGCAGGAAGAAAGATTAAAGGCTGC

AACTTTCACGAAAGCAAACTGGACTACTTTAACGAAATATTAGCTCT

GACACCCACGAATGCACCCTCCACGCTTACGAAAACGACATCATTGGC

TTCAACTGCCTGGAAACTACTCACCCAAACGAGGTTGAGGTTGAAGTT

GAAGACGCTGAAATCTACCTCCAGCCAGAGAACTGCTTCAACAACGTT

TACAAAGGCCTCAACAGCGTTGACATTACTACTATCCTGAAAAACGCT

CAGACCTACAACATCAACAACAAGAAAACCCCAACGTTCCTGAAAATT

CCGCCGTACAACCTGCTGGAAGACGTCGAAATTTCTTGTCAGTGCACT

ATTAAACAGGTTGTTAAAAAAATCAAAGTTATTATCACGAAAAACGAC

ACCGTTCTGCTGAAACGTGAAGTGCAGAGCGAGAGCACCCTGGACGAC

AAAATCTACAAATGCGAACACGAAAACTTCATTAACCCGCGTGTTAAC

AAAACCTTCGACGAAAACGTTGAATACACCTGCAACATCAAAATCGAG

AACTTTTTCAACTACATTCAGATCTTCTGCCCGGCCAAAGACCTCGGC

ATTTACAAAAACATCCAGATGTACTACGACATTGTTAAACCGACCCGT

GTTCCGCAGTTCAAAAAATTCAACAACGAAGAACTGCACAAACTGATT

CCAAACAGCGAAATGCTGCACAAAACCAAAGAAATGCTGATTCTGTAC

AACGAAGAAAAGTGGACCTCCTGCACTTCTACGTTTTTCTGCCGATC

TACATCAAAGATATCTACGAATTTAACATCGTTTGCGACAACAGCAAA

ACCATGTGGAAAAACCAGCTGGGCGGCAAAGTTATCTACCACATTACT

GTTAGCAAACGTGAGCAAAAAGTTAAAGGCTGCAGCTTCGACAACGAA

CACGCTCACATGTTCTCTTACAACAAAACTAACGTTAAAAACTGCATT

ATCGACGCTAAACCAAAAGACCTCATCGGCTTTGTTTGCCCTAGCGGC

ACGCTGAAACTGACCAACTGCTTCAAAGACGCTATCGTTCACACCAAC

CTGACCAACATTAACGGCATCCTCTACCTGAAAAACAACCTCGCTAAT

TTCACCTACAAACACCAGTTCAACTACATGGAAATCCCGGCTCTGATG

GACAACGACATCAGCTTCAAATGCATCTGCGTTGACCTGAAAAAAAAA

AAATACAACGTCAAAAGCCCGCTGGGCCCATGATAAGCGGCCGC
```

Here, the bold, underlined sequence refers to restriction enzyme sites to facilitate cloning into an expression plasmid vector.

In still other embodiments of the present invention, the codon harmonized gene corresponds to the nucleic acid sequence shown as SEQ ID NO: 12, where SEQ ID NO:12 corresponds to codon harmonized Pfs230 A4B5.

```
                                          SEQ ID NO: 12
CATATGGCACACCATCATCATCATCATCCCGGGGGATCCGGTTCTGGT

ACCAACCGTCACGTTTGCGACTTTAGCAAAAACAACCTGATTGTTCCG

GAAAGCCTGAAAAAAAAGAAGAGCTCGGCGGCAACCCGGTTAACATT

CACTGCTACGCTCTGCTGAAACCACTGGACACCCTGTACGTTAAATGC

CCAACCAGCAAAGACAACTACGAAGCTGCTAAAGTTAATATCAGCGAA

AATGATAACGAATACGAGCTGCAGGTTATCAGCCTGATAGAAAAACGT

TTCCACAACTTCGAGACGCTGGAATCGAAGAAACCAGGCAACGGCGAC

GTTGTTGTTCACAACGGCGTTGTTGACACTGGCCCAGTTCTGGACAAT

TCTACCTTCGAAAAATACTTCAAAAACATCAAAATCAAACCGGACAAA

TTCTTCGAGAAAGTTATCAACGAATACGACGACACTGAAGAAGAAAAA

GACCTGGAATCTATCCTGCCAGGGGCTATTGTTTCTCCAATGAAAGTT

CTGAAAAAAAGGACCCATTCACCAGCTACGCTGCTTTCGTTGTTCCG

CCGATTGTTCCTAAAGACCTGCACTTCAAAGTTGAATGCAACAACACC
```

-continued

GAATACAAAGACGAAAACCAGTACATCTCTGGCTACAACGGCATCATC

CACATTGACATCAGCAACTCTAACCGCAAAATTAACGGCTGCGACTTT

AGCACTAATAACTCTAGCATTCTGACCTCGTCTGTTAAACTGGTTAAC

GGCGAAACTAAAAACTGCGAAATCAACATCAACAACAACGAAGTTTTC

GGCATAATCTGCGACAACGAAACCAACCTGGACCCGGAAAAATGCTTC

CACGAAATCTACTCTAAAGACAACAAAACTGTTAAAAAATTCCGAGAA

GTTATCCCAAACATCGACATCTTTAGCCTGCACAACAGCAACAAGAAA

AAAGTTGCTTACGCTAAAGTTCCACTGGACTACATTAACAAACTGCTG

TTCAGCTGCAGCTGCAAAACCAGCCACACTAACACCATCGGCACGATG

AAAGTTACTCTCAACAAAGACGAAAAAGAAGAAGAAGACTTCAAAACC

GCTCAGGGCATTAAACACAACAACGTTCACCTGTGCAACTTTTTCGAC

AACCCAGAACTGACCTTCGACAACAACAAAATCGTTCTGTGCAAAATA

GACGCTGAATTATTTAGCGAAGTTATTATCCAGCTGCCGATCTTCGGC

ACCAAGAACGTTGAAGAAGGCGTTCAGAACGAAGAATACAAAAAATTC

AGCCTGAAACCGAGCCTGGTTTCGACGACAATAACAACGACATTAAAG

TTATCGGCAAAGAAAAAAACGAAGTTAGCATTTCTCTGGCTCTCAAAG

GGGTTTACGGCAACCGAATTTTCACTTTCGACAAAAACGGCAAAAAAG

GCGAAGGCATTTCTTTCTTCATCCCACCGATCAAACAGGACACCGACC

TGAAATTCATCATTAACGAAACCATCGACAACAGCAACATTAAACAGC

GTGGCCTGATCTACATTTTCGTTCGCAAAAACGTTAGCGAAAACAGCT

TCAAACTGTGCGACTTTACCACCGGCTCGACTAGCCTGATGGAACTGA

ACTCTCAGGTTAAAGAAAAAAAGTGTACTGTTAAAATTAAAAAAGGCG

ACATTTTCGGCCTCAAATGCCCAAAAGGCTTCGCTATCTTCCCGCAGG

CTTGCTTCTCTAACGTTCTGCTGGAATACTACAAATCTGACTACGAAG

ACTCTGAACACATTAACTACTACATTCACAAAGACAAAAAATACAACC

TGAAACCAAAAGACGTTATTGAACTGATGGACGAAAACTTCCGTGAAC

TGCAGAACATCCAGCAGTACACCGGCATCAGCAACATTACCGACGTGC

TGCACTTTAAAAACTTCAACCTGGGCAACCTCCCGCTGAACTTCAAAA

ACCACTACAGCACCGCTTACGCTAAAGTTCCGGACACGTTCAACAGCA

TTATTAATTTTAGCTGCAACTGCTACAACCCGGAAAAACACGTTTACG

GCACTATGCAGGTTGAGAGCGACAACTGATAAGCGGCCGC

Here, the bold, underlined sequence refers to restriction enzyme sites to facilitate cloning into an expression plasmid vector.

In other embodiments of the present invention, the codon harmonized gene corresponds to the nucleic acid sequence shown as SEQ ID NO: 13, where SEQ ID NO: 13 corresponds to codon harmonized Pfs230 A6B7.

SEQ ID NO: 13

CATATGGCACACCATCATCATCATCATCCCGGGGGATCCGGTTCTGGT

ACCAACGAACACATCTGCGACTACGAAAAAAACGAAAGCTTAATCAGC

ACCCTGCCAAACGACACCAAAAAAATCCAGAAATCTATATGCAAAATT

AACGCTAAAGCTCTGGACGTTGTTACCATTAAATGCCCACACACCAAA

AACTTCACGCCAAAAGACTACTTCCCAAACAGCAGCCTGATCACTAAC

GACAAAAAAATTGTGATTACTTTCGACAAGAAAAACTTCGTTACTTAC

ATCGACCCAACCAAAAAAACCTTCAGCCTCAAAGACATCTACATCCAG

TCTTTCTACGGCGTTAGCCTCGACCACCTCAACCAGATCAAAAAAATC

CACGAAGAATGGGACGACGTTCACCTGTTCTACCCACCACACAACGTT

CTGCACAACGTTGTTCTCAACAACCACATCGTCAATCTGAGCAGCGCT

CTGGAAGGCGTCCTGTTCATGAAAAGCAAAGTTACTGGCGACGAAACC

GCTACCAAAAAAAATACTACCCTCCCGACTGACGGCGTTAGCTCTATT

CTGATTCCGCCGTACGTTAAGGAAGACATCACCTTCCACCTCTTCTGC

GGGAAAAGCACCACCAAAAAACCGAATAAAAAGAATACCAGCCTCGCT

CTCATTCACATCCACATCAGCAGCAATCGTAACATTATTCACGGCTGC

GACTTTCTGTACCTGGAAAACCAGACCAACGACGCTATTTCTAACAAC

AACAACAACAGCTACAGCATCTTCACCCACAACAAAAACACCGAGAAC

AACCTCATCTGCGACATCAGCCTGATTCCGAAAACTGTTATCGGCATT

AAATGCCCAAACAAAAAACTGAACCCGCAGACCTGCTTCGACGAAGTG

TACTACGTTAAACAGGAAGACGTTCCATCGAAAACTATCACCGCTGAC

AAATACAACACCTTCTCTAAAGATAAAATCGGCAACATCCTGAAAAAC

GCTATAAGCATTAACAACCCGGACGAAAAGGACAACACCTACACTTAC

CTGATCCTGCCGGAAAAATTCGAAGAAGAACTGATAGACACGAAAAAA

GTTCTGGCTTGCACCTGCGACAACAAATACATCATCCACATGAAAATC

GAAAAATCTACCATGGACAAAATCAAAATCGACGAAAAAAAAACCATT

GGCAAAGACATCTGCAAATACGACGTTACTACTAAAGTTGCTACTTGC

GAAATTATTGACACCATTGACTCGAGCGTTCTGAAAGAACACCACACC

GTTCACTACAGCATTACCCTGAGCCGTTGGGACAAACTCATTATTAAA

TACCCGACCAACGAGAAAACCCACTTTGAAAACTTCTTCGTTAACCCA

TTCAACCTGAAAGACAAAGTTCTGTACAACTACAACAAACCGATCAAC

ATCGAACACATACTGCCGGGCGCCATTACCACCGACATCTACGACACG

CGTACCAAAATTAAACAGTACATCCTGCGTATTCCGCCGTACGTTCAC

AAAGACATCCACTTTAGCCTGGAATTCAATAACTCGCTCTCTCTGACC

AAACAGAACCAGAACATTATTTACGGCAACGTTGCCAAAATTTTCATT

CACATCAACCAGGGCTACAAAGAAATTCACGGCTGCGACTTTACCGGC

AAATACTCGCACCTGTTCACCTACAGCAAAAAACCACTGCCGAACGAC

GACGACATCTGCAACGTTACTATCGGCAACAACACCTTTAGCGGCTTC

GCTTGTCTGTCGCACTTCGAACTGAAACCGAACAATTGTTTTAGCAGC

GTTTACGACTACAACGAAGCCAACAAAGTTAAAAAACTGTTTGACCTC

TCGACCAAAGTTGAACTGGATCACATAAAACAGAACACTAGCGGCTAC

ACCCTCAGCTACATTATTTTCAACAAAGAATCGACCAAACTCAAATTT

AGCTGCACCTGTAGCTCGAATTACAGCAACTACACTATCCGAATAACC

TTCGACCCATGATAAGCGGCCGC

Here, the bold, underlined sequence refers to restriction enzyme sites to facilitate cloning into an expression plasmid vector.

The compositions of the invention are designed for expression in a host. In preferred embodiments, a host is *E. coli* or an *E. coli* derivative. The DNA encoding the desired recombinant protein can be introduced into a host cell in any suitable form including, the fragment alone, a linearized plasmid, a circular plasmid, a plasmid capable of replication, an episome, RNA, etc. Preferably, the gene is contained in a plasmid. In a particularly preferred embodiment, the plasmid is an expression vector. Individual expression vectors capable of expressing the genetic material can be produced using standard recombinant techniques. Please see e.g., Maniatis et al., 1985 Molecular Cloning: A Laboratory Manual or DNA Cloning, Vol. I and II (D. N. Glover, ed., 1985) for general cloning methods Accordingly, the present invention contemplates host cells transformed with a vector as described herein. For example, the vector may comprise a codon harmonized Pfs48/45 sequence suitable for expression in a cell, a codon harmonized Pvs48/45 sequence suitable for expression in a cell, a codon harmonized Pfs25 sequence suitable for expression in a cell.

The one or more *Plasmodium* pre-fertilization or post-fertilization antigens, for example *Plasmodium falciparum* or *Plasmodium vivax* pre-fertilization or post-fertilization antigens can be used singly, or in combinations. For example, a combination may comprise antigens derived from different *Plasmodium* species that will be capable of blocking the infection and/or transmission of more than one *Plasmodium* species. For example, an immunogenic composition comprising Pfs48/45 and Pvs48/45 will be capable of blocking the transmission of both *P. falciparum* and *P. vivax*.

METHODS OF THE INVENTION

The present invention describes an approach that harmonizes codon usage frequency of the target gene with those of the expression host for heterologous expression of protein. Basic studies on regulation of protein expression have shown that synonymous codon substitutions from infrequent to frequent usage in regions where mRNA translation occurs relatively slowly can be detrimental to protein expression and stability [17]. On the other hand, codon substitutions introducing rare codons in the regions containing high frequency codons can lead to erroneous protein conformation [18]. Taking these concepts into account, an algorithm termed "codon harmonization" [19] was developed where synonymous codons from *E. coli* were selected that closely resemble the codon usage of native Pfs48/45 gene, including regions coding 'link/end' segments of proteins in *P. falciparum*. This approach harmoniously mimics the translation rate of protein expression in native host by allowing the translation machinery to pause at exactly the same positions in *E. coli* as in *P. falciparum* and yield expression of correctly folded protein, for example, Pfs48/45 in *E. coli*.

The present invention describes for the first time the efficient and successful expression of a pre-fertilization antigen, and in particular, full length TBV candidate Pfs48/45, in high yields and appropriate conformation. The recombinant Pfs48/45 elicits potent malaria transmission blocking antibodies in mice and non human primates (Olive baboons, *Papio anubis*) and indicates the development of a malaria TBV based on the CH-rPfs48/45 antigen.

In certain preferred embodiments of the invention, the pre-fertilization or post-fertilization antigens can be used to develop malaria transmission-blocking immunogenic compositions. Accordingly, the invention features methods of blocking transmission of *Plasmodium falciparum* or *Plasmodium vivax* in a subject comprising administering to a subject an immunogenic composition comprising one or more *Plasmodium falciparum* or *Plasmodium vivax* pre-fertilization or post-fertilization antigens, thereby blocking transmission of *Plasmodium falciparum* or *Plasmodium vivax* in the subject.

In certain embodiments, it may be desirable to measure transmission, for example, by measuring the reduction of mosquito oocysts by sera or plasma from a subject treated with the immunogenic composition compared to a control subject. Accordingly, pre-immune sera from the treated subject and the control subject are used as a measure of 100% transmission for the corresponding test sera.

The invention also features methods of immunizing a subject against *Plasmodium falciparum* or *Plasmodium vivax* comprising administering to a subject an immunogenic composition comprising one or more *Plasmodium falciparum* or *Plasmodium vivax* pre-fertilization or post-fertilization antigens, and thereby immunizing the subject against *Plasmodium falciparum* or *Plasmodium vivax*.

The immunogenic compositions of the invention are also preferably used in methods for treating or preventing malaria in a subject comprising administering to a subject an immunogenic composition comprising one or more *Plasmodium falciparum* or *Plasmodium vivax* pre-fertilization or post-fertilization antigens, thereby preventing malaria in the subject.

In preferred embodiments, the pre-fertilization or post-fertilization antigens can be classified as *Plasmodium falciparum* or *Plasmodium vivax* surface antigens. In certain preferred embodiments, the surface antigens are gametocyte or gamete surface antigens. Exemplary gametocyte or gamete surface antigens are selected from the group consisting of Pfs48/45, Pfs230, Pvs48/45 and Pvs230. In other embodiments, the surface antigens are midgut parasite surface antigens. Exemplary midgut parasite surface antigens are selected from the group consisting of Pfs25, Pfs28, Pvs25 and Pvs28.

Preferably, the one or more pre-fertilization or post-fertilization antigens are selected from the group consisting of Pfs48/45, Pfs 230, Pfs25, Pvs48/45, Pvs 230 and Pvs25. In particular, in certain embodiments, the pre-fertilization antigen is Pfs48/45. In other embodiments, the post-fertilization antigen is Pfs25.

As described herein, codon harmonized genes are preferably employed in the methods of the invention, where, generally, a wild type nucleic acid sequence encoding a polypeptide is modified to enhance expression and accumulation of the polypeptide in the host cell by harmonizing synonymous codon usage frequency between the foreign DNA and the host cell DNA. Accordingly, in certain preferred embodiments, of the invention, one or more pre-fertilization antigens or post-fertilization antigens is derived from a codon harmonized gene.

Codon harmonized genes are described herein, and in particular embodiments the modified (codon harmonized) nucleic acid sequence and/or the encoded polypeptide are shown in SEQ ID NOs 1-SEQ ID NO: 13.

Administration

The immunogenic compositions of the present invention can be administered to a subject by different routes such as subcutaneous, intradermal, intramuscular, intravenous and transdermal delivery. Suitable dosing regimens are preferably determined taking into account factors well known in the art including age, weight, sex and medical condition of the subject; the route of administration; the desired effect; and the particular composition.

The course of the immunization may be followed by assays for activated T cells produced, skin-test reactivity, antibody formation or other indicators of an immune response to a malarial strain.

Dosage form, such as injectable preparations (solutions, suspensions, emulsions, solids to be dissolved when used, etc.), tablets, capsules, granules, powders, liquids, liposome inclusions, ointments, gels, external powders, sprays, inhalation powders, eye drops, eye ointments, and the like, can be used appropriately depending on the administration method. Pharmaceutical formulations are generally known in the art and are described, for example, in Chapter 25.2 of Comprehensive Medicinal Chemistry, Volume 5, Editor Hansch et al, Pergamon Press 1990.

Pharmaceutically acceptable carriers which can be used in the present invention include, but are not limited to, an excipient, a stabilizer, a binder, a lubricant, a colorant, a disintegrant, a buffer, an isotonic agent, a preservative, an anesthetic, and the like which are commonly used in a medical field.

Immunogenic compositions are administered in immunologically effective amounts. An immunologically effective amount is one that stimulates the immune system of the subject to establish a level of immunological response sufficient to reduce parasite density and disease burden caused by infection with the pathogen, and/or sufficient to block the transmission of the pathogen in a subject.

A dose of the immunogenic composition may, in certain preferred embodiments, consist of the range of 1 µg to 1.0 mg total protein. In certain preferred embodiments, the composition is administered in a concentration between 1-100 µg. However, one may prefer to adjust dosage based on the amount of antigen delivered. In either case these ranges are guidelines. More precise dosages should be determined by assessing the immunogenicity of the composition so that an immunologically effective dose is delivered. The immunogenic composition can be used in multi-dose formats.

The timing of doses depends upon factors well known in the art. After the initial administration one or more booster doses may subsequently be administered to maintain antibody titers, e.g., the compositions of the present invention can be administered one time or serially over the course of a period of days, weeks, months and or years. An example of a dosing regime would be day 1 an additional booster doses at distant times as needed. The booster doses may be administered at 2, 3, 4, 5, 6, 7, 8, 9, 10, 11, 12, 13, 14, 15, 16, 17, 18, 19, 20 or more weeks after the primary immunization. In preferred embodiments, the booster doses are administered at 4 weeks. In other preferred embodiments, the booster doses are administered at 12 weeks.

In other cases, the immunogenic compositions are administered after, before or at the same time as treatment with an additional agent, such as an agent to treat or prevent malaria.

As used herein the subject that would benefit from the immunogenic compositions described herein include any host that can benefit from protection against malarial infection. Preferably, a subject can respond to inoculation with the immunogenic compositions of the present invention by generating an immune response. The immune response can be completely or partially protective against symptoms caused by infection with a pathogen such as *Plasmodium falciparum*, or can block transmission of the pathogen by *Anopheles* mosquitoes. In a preferred embodiment, the subject is a human. In another embodiment, the subject is a non-human primate.

Formulations

The immunogenic compositions of the present invention can be used to immunize mammals including humans against infection and/or transmission of malaria parasite, or to treat humans post-infection, or to boost a pathogen-neutralizing immune response in a human afflicted with infection of malaria parasite.

The immunogenic compositions of the present invention can be formulated according to methods known and used in the art. Guidelines for pharmaceutical administration in general are provided in, for example, Modern Vaccinology, Ed. Kurstak, Plenum Med. Co. 1994; Remington's Pharmaceutical Sciences 18th Edition, Ed. Gennaro, Mack Publishing, 1990; and Modern Pharmaceutics 2nd Edition, Eds. Banker and Rhodes, Marcel Dekker, Inc., 1990. Immunogenic compositions of the present invention can be prepared as various salts. Pharmaceutically acceptable salts (in the form of water- or oil-soluble or dispersible products) include conventional non-toxic salts or the quaternary ammonium salts that are formed, e.g., from inorganic or organic acids or bases. Examples of such salts include acid addition salts such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate; and base salts such as ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as histidine, arginine and lysine.

Adjuvants are almost always required to enhance and/or properly direct the immune response to a given antigen. An ideal adjuvant should be safe, stable with long shelf life, biodegradable, inexpensive and promote an appropriate immune response while itself being immunologically inert. Adjuvants affect processes including antigen presentation, antigen uptake and selective targeting of antigens thus critically determining the magnitude and type of the immune responses [34-36]. While the mechanisms by which different adjuvants result in different outcomes remain a "black box", studies strive for developing a vaccine that can provide maximum efficacy with ease of delivery in as fewer doses as possible. It must be kept in mind that an adjuvant is not the active component in a vaccine and immunization; outcomes can vary greatly from one adjuvant to another when used in combination with the same vaccine antigen. Any given adjuvant-vaccine combination has to be evaluated on a case-by-case basis for safety, reactogenicity and efficacy in pre clinical trials. Ultimately, safety considerations outweigh any anticipated benefit and need to be evaluated for the development of a plan leading to human clinical trial [37].

Although aluminum compounds have been used for human vaccines since 1926, the need for developing new and more effective adjuvants has been felt increasingly for many other subunit and DNA vaccines, especially since the alum salts are relatively poor adjuvants [38]. Other experimental adjuvants used in a limited number of studies in humans include Quil A-derived saponin QS-21, bacterial and fungal derived moieties (e.g. muramyl dipeptide, monophosphoryl lipid A, CpG etc.), Water-in-oil emulsions (e.g., MF59, FIA, Montanide), particulate delivery systems (e:g., VLPs, liposomes, microspheres, ISCOM).

In certain preferred embodiments, the immunogenic compositions are formulated with an aluminum adjuvant. Aluminum based adjuvants are commonly used in the art and include aluminum phosphate, aluminum hydroxide, aluminum hydroxy-phosphate, and amorphous aluminum hydroxyphosphate sulfate. Trade names of aluminum adjuvants in common use include ADJUPHOS, ALHYDROGEL, (both from Superfos Biosector a/s, DK-2950 Vedbaek, Denmark).

Non-aluminum adjuvants can also be used. Non-aluminum adjuvants include, but are not limited to, QS21, Lipid-A, Iscomatrix., and derivatives or variants thereof, Freund's complete or incomplete adjuvant, neutral liposomes, liposomes containing vaccine and cytokines or chemokines.

Emulsions of Montenide ISA 51 (a mineral oil adjuvant) and ISA 720 (oil-based non mineral oil) have been used in human clinical trials. A review of clinical trials (25 trials representing more than 4000 patients and 40,000 injections for Montanide ISA 51 and various trials representing 500 patients and 1500 injections for Montanide ISA 720) has revealed their general safety and strong adjuvant effect with mild to moderate local reactions.

In certain preferred embodiments of the invention, the method of the invention further comprises administering an adjuvant. In certain examples, the adjuvant is selected a water-in-oil emulsion. In other examples, the adjuvant is Aluminum hydroxide. However, any adjuvant that is suitable for administration with the immunogenic composition in the methods of the present invention can be suitably used.

Kits

Also included within the scope of the present invention are kits suitable for providing compositions of the immunogenic compositions as described herein.

For example, in such a kit one vial can comprise the immunogenic composition comprising one or more *Plasmodium falciparum* or *Plasmodium vivax* pre-fertilization or post-fertilization antigens, and instructions for use in reducing transmission of *Plasmodium falciparum* or *Plasmodium vivax*.

In another example, a kit can preferably comprise one or more *Plasmodium falciparum* or *Plasmodium vivax* pre-fertilization or post-fertilization antigens, and instructions for use in preventing malaria.

Preferably, the one or more pre-fertilization or post-fertilization antigens are selected from the group consisting of Pfs48/45, Pfs230, Pfs 28, Pfs25, Pvs48/45, Pvs 230, Pvs 28, and Pvs25. In exemplary embodiments, the one or more pre-fertilization or post-fertilization antigens is derived from a codon harmonized gene.

Preferably, the kit will contain instructions for using the composition. Such instructions can be in the form of printed, electronic, visual, and or audio instructions.

EXAMPLES

Example 1

Expression and Purification of Correctly Folded Pfs48/45

Generally speaking it is often difficult to express *P. falciparum* proteins in a heterologous expression system and such problems are largely due to high A/T content giving rise to changes in codon usage frequencies. It is now increasingly being realized that synonymous codon substitutions are not always silent and changes in the frequency of codon usage affects protein structure and function. Differences in synonymous codon usage between expression and natural hosts greatly affect expression and stability of proteins. These codon differences have even greater consequences if they occur infrequently and within the domains that encode polypeptide regions of higher ordered structure. The presence of infrequently used codons is believed to cause ribosome pausing leading to incorrect folding and premature termination of protein during translation. An algorithm that takes into account known relationships between codon usage frequencies and secondary protein structure (designated codon harmonization algorithm) [25] has been developed to identify regions of slowly translated mRNA that are putatively associated with 'link/end' polypeptide segments contributing to higher ordered structures in a protein. Thus modification of those 'link/end' region codons and other codons to match the frequency in the expression host can counter non-natural ribosomal pausing and allow for co-translational folding, of proteins as synthesis continues [25]. By allowing the translation machinery to slow or pause at the same position in the transcript in the expression host as in the natural host (i.e. *Plasmodium*), the secondary structures in the nascent proteins are formed at comparable rates and thus lead to proper conformational folding and solubility of the expressed protein.

The native sequence of Pfs48/45 is represented by NCBI accession number AF356146, corresponding to SEQ ID NO: 7.

Here, the native sequence of Pfs 48/45 as represented by SEQ ID NO: 7, lacking N-terminal signal sequence (amino acid residues 1-27) and C-terminal anchor (amino acid residues 428-448) was converted to 'codon harmonized' sequence designed for expression in *E. coli*. The amino acid sequence reported under AF356146 differs from that of Z22145 (NF54) by C32Y, K33N, T72N, K253N and N254K substitutions. The A/T contents of Pfs48/45 sequence before and after codon harmonization were 75% and 56%, respectively. The codon harmonized Pfs48/45 sequence containing a sequence tag coding for 6× histidines at the 5' end was synthesized and cloned into the pET (K-) expression vector [19] and expressed in BL21 (DE3) cells [FIG. 1*a*]. Initial attempts to induce the cells with IPTG indicated that the expressed protein might negatively impact the growth of *E. coli*. To overcome the toxicity of expressed protein, the expression strategy was modified to slow down protein expression by growing the cells at 30° C. in Luria-Bertani growth medium containing 1% glucose and induction with 0.1 mM IPTG for 3 h, which resulted in highly efficient induction of protein in the cell lysate at 50 kDa [FIG. 1*b*, left panel, encircled]. The cell lysate when treated with β-ME to reduce the disulphide bonds in the protein, showed slower electrophoretic mobility of the induced Pfs48/45 protein [FIG. 1*b*, right panel, encircled]. A similar observation was made with the native form of the protein on the gametocyte surface [22,23].

Figure 1F:
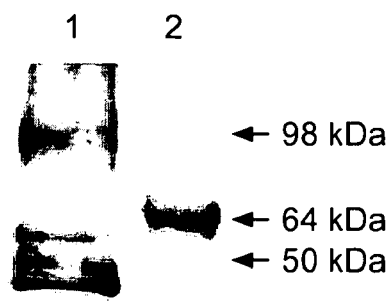

Western blot analysis of cell lysates either untreated or after treatment with 0.5% sarcosyl revealed that the recombinant protein was insoluble in the absence of sarcosyl detergent (data not shown), and hence the treatment with ionic detergent was required to facilitate extraction of the protein from the pellet. To selectively enrich expressed Pfs48/45, the lysate was first treated with non-ionic detergent Tween-80 to remove any soluble bacterial proteins followed by treatment with 0.5% sarcosyl in PBS [FIG. 1*c*]. This sequential detergent extraction resulted in partial solubilization of the expressed protein which could be further purified using Ni2+-NTA-Agarose beads (QIAGEN) by elution using imidazole (1 M), yielding ~3 mg purified protein/g of wet cell pellet [FIG. 1*d, e*]. The yield of purified CH-rPfs48/45 in 7 independent purifications varied between 15 and 25 mg per liter of induced culture. The conformational characterization of the expressed protein designated CH-rPfs48/45 was achieved using a mAb IIC5-B10 [22], which recognizes a conformational reduction-sensitive epitope in the parasite derived native Pfs48/45. The mAb recognized the non-reduced form of CH-rPfs48/45 yielding 3 immunoreactive bands at ~50 kDa of the gel [FIG. 1f, lane 1]. In addition to these monomeric forms, purified CH-rPfs48/45 protein preparations consistently revealed the presence of a higher molecular weight band at ~98 kDa, presumed to be a dimer. When a similar Western blot analysis was carried out with CH-rPfs48/45 after reduction prior to SDS-PAGE, the mAb rather unpredictably showed recognition of a single band around 65-68 kDa [FIG. 1f, lane 2]. Previous biosynthetic metabolic labeling studies had established that non-reduced Pfs48/45 immunoprecipitated by the mAb IIC5B10 (a doublet migrating in the region of 45 and 48 kDa) coalesces into a single protein band of ~68 kDa when analyzed by SDS-PAGE after reduction [23]. On the other hand, the same mAb recognized only the non-reduced form of native Pfs48/45 in the gametocytes and gametes in Western blot analysis [24]. While the reasons for the totally unexpected recognition of reduced form of CH-rPfs48/45 are not so obvious, a possible interpretation may be that the functional target epitope of blocking antibodies might be conformationally more stable in the CH-rPfs48/45, and therefore not affected by the reduction conditions employed.

Example 2

Figure 2A:
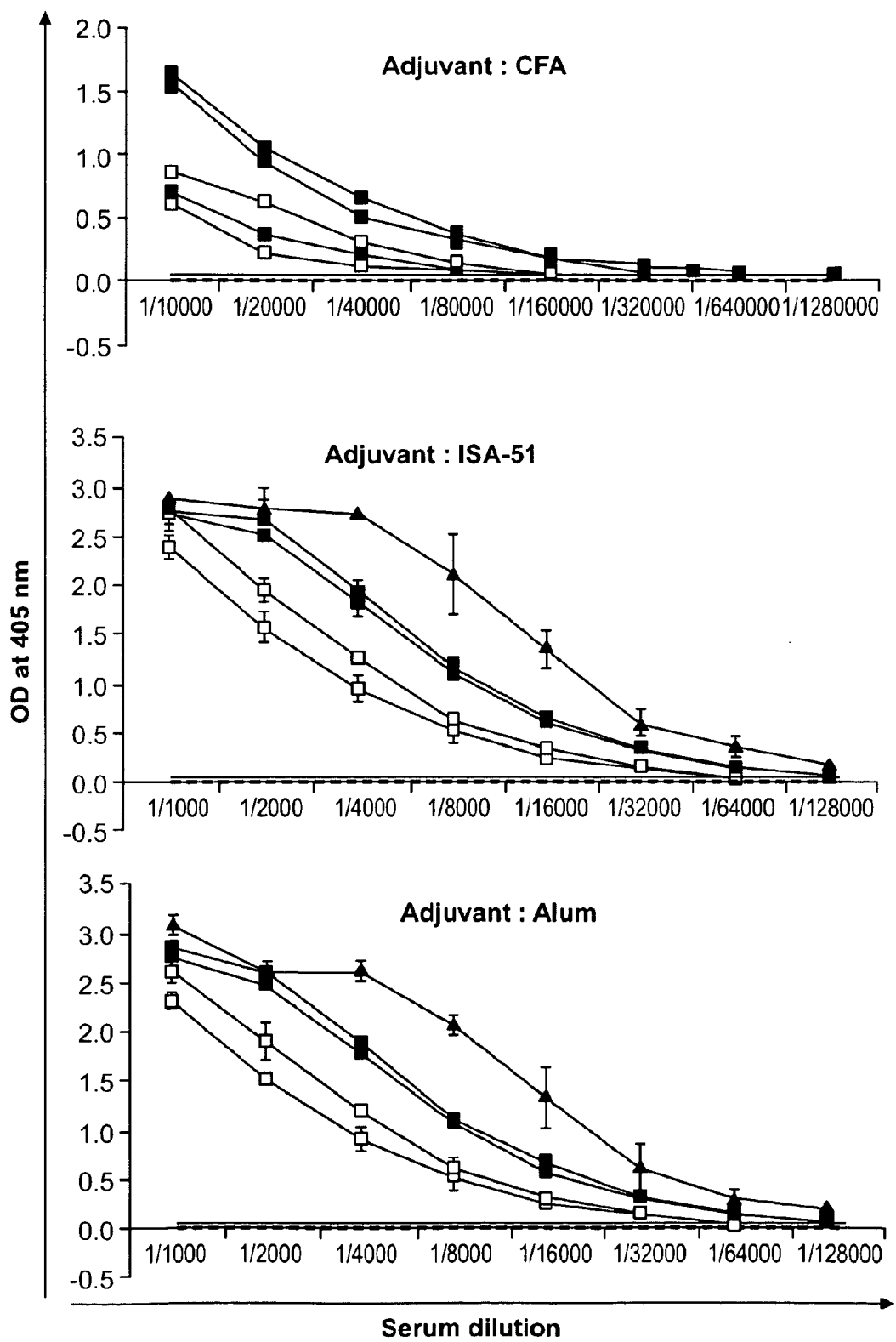
FIG. 2 (*a* & *b*) is two panels that show (a) ELISA analysis of CH-rPfs48/45 immunized individual mouse sera in three different adjuvant formulations: Complete Freund's adjuvant (top panel), Montanide ISA-51 (middle panel), and Alum (bottom panel). All the results are representative of three independent experiments. Pooled pre-immune sera+3SD are shown by broken lines. ELISA OD405 values for individual mice are shown; mouse 1 (filled triangle), mouse 2 (open square), mouse 3 (filled square), mouse 4 (open circle), mouse 5 (filled circle). (b) Analysis of anti-Pfs48/45 IgG isotype distribution in individual mouse sera: IgG1 (filled columns), IgG2a (hatched columns), IgG2b (stippled columns), IgG3 (blank columns).
Figure 2B:
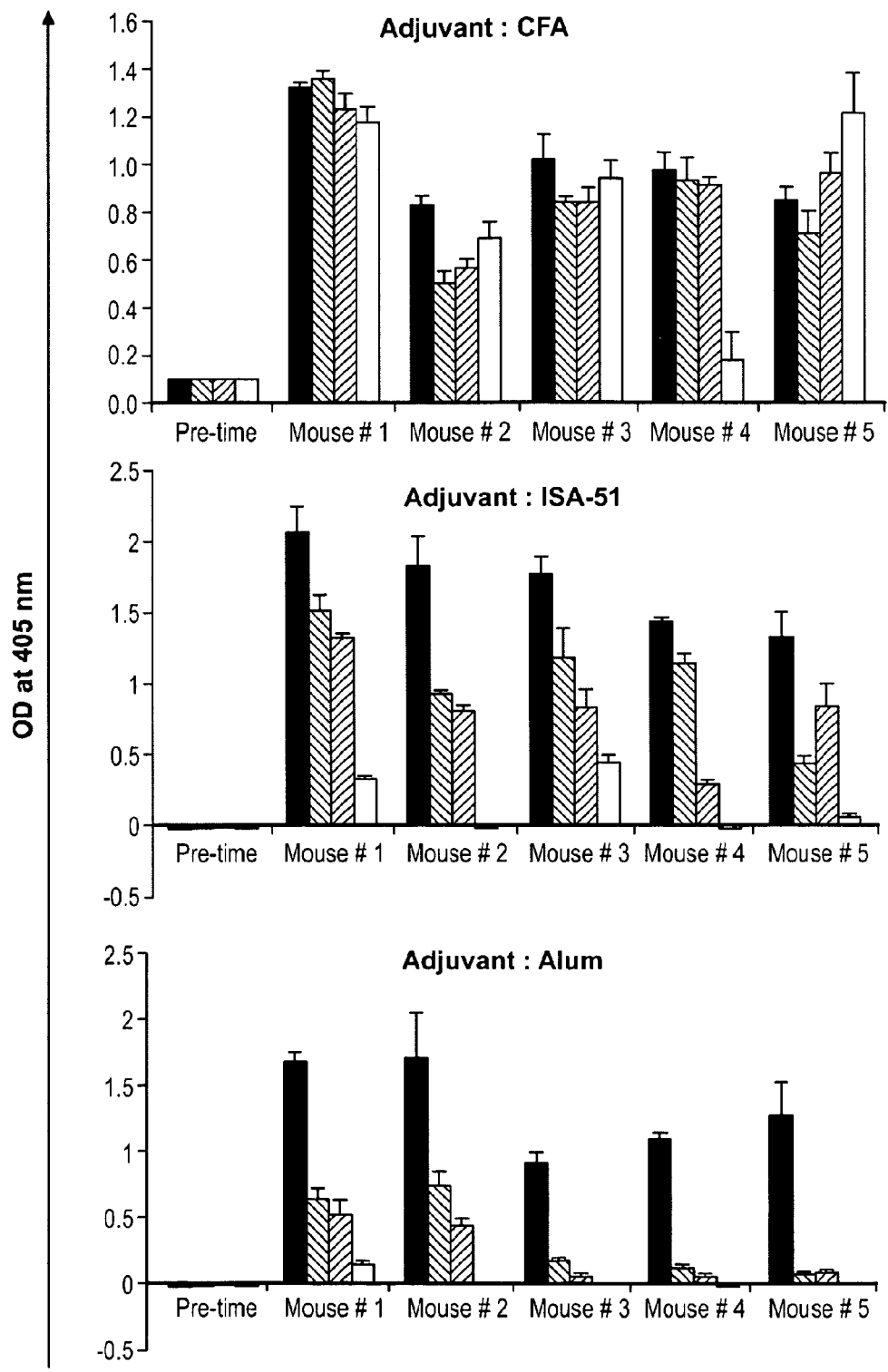

Evaluation of Functional Immunogenicity of CH-rPfs48/45 in Mice in Different Adjuvant Formulations The immunogenicity of CH-rPfs48/45 was assessed in three different adjuvant formulations: CFA, water-in-oil emulsion using Montanide ISA-51 and Aluminium hydroxide. FIG. 2a shows the IgG titer 2 weeks after the 2nd boost in CFA group and 2 weeks after the 3rd boost in Alum and Montanide ISA-51 groups. This formulation resulted in the highest antibody titer ranging from $3 \times 10^5$ to $>1 \times 10^6$ [FIG. 2a, top panel]. However, all mice immunized with CH-rPfs48/45 in the other two adjuvant formulations also showed high antibody titer, the range being ~70,000 to more than 100,000 in both Montanide ISA-51 and Alum formulations [FIG. 2a, middle and bottom panels]. Sera for IgG isotype distribution was also tested and all four subtypes (IgG1, IgG2a, IgG2b, IgG3) were more or less equally represented in sera from mice immunized with CFA formulation, [FIG. 2b, top panel]. On the other hand, IgG1 and to a lesser extent IgG2 were the dominant subtype in Montanide ISA-51 formulation [FIG. 2b, middle panel]. The overwhelming presence of IgG1 and negligible amount of IgG3 were noticed in the Alum formulation [FIG. 2b, bottom panel].

Figure 3A:
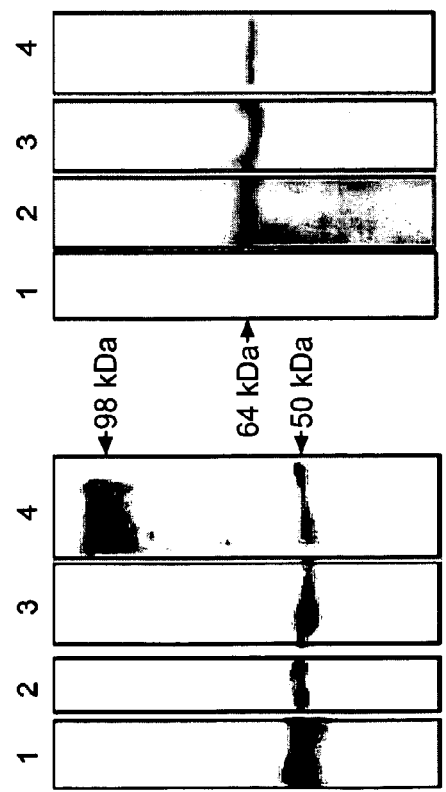
FIG. 3 (*a* & *b*) shows recognition of native Pfs48/45 in *P. falciparum* gametocyte extract. (a) Western blot analysis with non-reduced (left panel) or reduced (right panel) *P. falciparum* gametocyte extract against serum of individual mouse immunized with either CFA or ISA-51 or alum formulation. Stage V gametocyte extract was run either in non-reduced or reduced (10 mM 2-mercaptothanol) form in SDS-PAGE and transferred to nitrocellulose membrane. Mice sera were allowed to react at 1:1000 dilution for 1 h at 22° C. HRP-conjugated anti-mouse IgG at 1:10000 dilution was used as detection antibody and was developed using ECL substrate. Lane 1, mAb IIC5B10; lane 2, one representative mouse serum immunized in CFA; lane 3, one representative mouse serum immunized in Montanide ISA-51; lane 4, one representative mouse serum immunized in alum formulation. The figure is assembled from separate experiments. (b) Mouse sera (1:1000 dilution) were tested by live immunofluorescence assays as described under materials and methods.
Figure 3B:
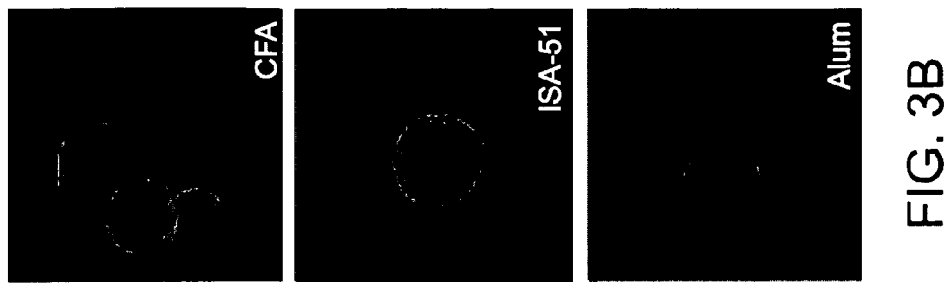

Individual mouse sera were also tested for their ability to recognize the native Pfs48/45 protein in gametocyte extracts in both reduced and non-reduced form in Western blot analysis. Polyclonal antisera against CH-rPfs48/45 recognized a combination of reduction-sensitive as well as reduction-insensitive epitopes in Pfs48/45 in the parasites. Sera from mice immunized with CFA and ISA-51 formulations recognized the native non reduced protein (48/45 kDa), however, the sera from mice immunized with alum formulation revealed recognition of 48/45 kDa protein and also a protein ~98 kDa [FIG. 3a, left panel]. The reduced form of the native protein was recognized by all of the aforementioned sera at ~64 kDa [FIG. 3a, right panel]. As previously demonstrated [24] the mAb IIC5B10 reacted only with nonreduced native parasite antigen. The ability of the anti-CH-rPfs48/45 sera to recognize the native form of the protein was further tested by live immunofluorescence assay (IFA) using live extracellular gametes. FIG. 3b shows an example of strong gamete surface reactivity typical of that observed for sera from mice immunized with CH-rPfs48/45 in all three adjuvant groups.

To assess the functionality of the immunized sera, they were tested for transmission blocking activity in mosquitoes in membrane feeding assays (MFA) [10]. All the mice sera in the three adjuvant groups showed a strong (>98% reduction in the number of oocysts) transmission blocking activity at 1:2 dilution [Table 1, shown below] as compared to corresponding pre-immune sera.

TABLE 1

| Animal no. | Serum dilution | | |
|---|---|---|---|
| | 1:2 | 1:4 | 1:8 |
| CFA | | | |
| 1 | 100.0 (0/20) | 89.6 (8/20) | 76.8 (18/33) |
| 2 | 97.5 (14/41) | 88.0 (7/16) | 79.3 (24/38) |
| 3 | 98.3 (7/28) | 90.2 (4/15) | 72.6 (16/34) |
| 4 | 94.3 (12/22) | 90.5 (9/26) | 83.5 (21/42) |
| 5 | 98.0 (9/30) | 93.9 (6/20) | 84.6 (15/28) |
| ISA 51 | | | |
| 6 | 96.1 (5/15) | 88.0 (16/23) | 76.8 (12/19) |
| 7 | 98.4 (2/12) | 89.9 (11/20) | 74.9 (10/17) |
| 8 | 96.4 (7/18) | 92.5 (12/22) | 69.7 (16/22) |
| 9 | 96.2 (7/15) | 90.6 (15/25) | 72.6 (11/18) |
| 10 | 95.1 (10/20) | 86.2 (10/17) | 79.1 (12/19) |
| Alum | | | |
| 11 | 93.5 (11/24) | 86.2 (14/30) | 54.9 (21/29) |
| 12 | 95.3 (9/26) | 78.6 (16/24) | 58.3 (14/20) |
| 13 | 96.6 (12/31) | 89.9 (6/15) | 55.4 (15/22) |
| 14 | 94.5 (7/16) | 89.2 (9/17) | 70.5 (16/26) |
| 15 | 95.2 (5/16) | 91.6 (6/16) | 61.4 (16/23) |

Table 1 shows MFA with sera from mice immunized with CH-rPfs48/45 formulated in CFA, Montanide ISA-51 or Alum. Individual mouse sera were tested for transmission blocking activity with respect to corresponding pooled pre-immune sera. Data are represented as percent transmission blocking activity (reduction in the number of oocysts per mosquito midgut). Numbers within parenthesis represent total number of infected mosquitoes/total number of mosquitoes dissected for each feed.

Geometric mean oocyst numbers per midgut in the presence of pooled pre-immune sera of mice immunized in various adjuvant formulations and tested at different dilutions ranged between 10.4 and 16.7. The decrease in oocyst number/midgut by each immune sera was significant ($P<0.02$, Mann-Whitney test).

The transmission blocking effect was dependent upon the antibody dose as revealed by a gradual decrease with increasing sera dilutions. Sera from mice immunized with CH-rPfs48/45 vaccine in CFA and Montanide ISA-51 formulations as compared to Alum appeared to be relatively more potent blockers as apparent from the stronger transmission blocking activities at 1:8 dilution of sera in MFA.

Example 3

Evaluation of Functional Immunogenicity of CH-rPfs48/45 in Non Human Primates (Olive Baboons)

Backed by strong functional immunogenicity of CH-rPfs48/45 in three different adjuvant formulations in mice, the CH-rPfs48/45 vaccine was next evaluated in non-human primates (*Papio anubis*, Olive baboons). The vaccine trial in baboons was approved by the institutional and scientific review committee of the Institute of Primate Research with a protocol #19/10/2007.

Figure 4A:
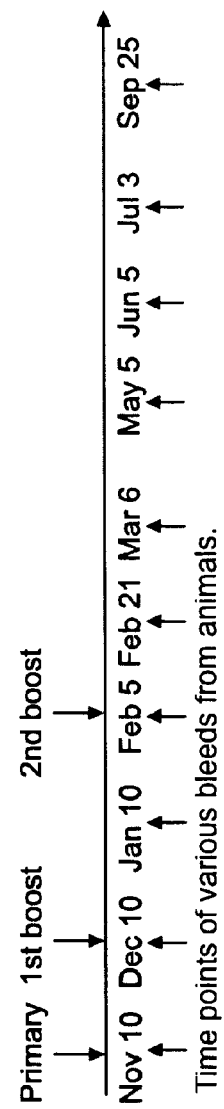
FIG. 4 (a-c) shows analysis of anti-Pfs48/45 antibody production by Olive baboons (Papio anubis). (a) Each animal was immunized with CH-rPfs48/45 (50 μg in 0.25 ml endotoxin free PBS) formulated in Montanide ISA-51 (0.25 ml) in baboons, administered intra muscularly (quadriceps, two sites). Schedules for immunization and bleeds are indicated and sera were stored at −20° C. until shipped frozen from Kenya to Baltimore for ELISA and MFA. The samples were shipped under an export permit CITES #008101. (b) Anti-Pfs48/45 whole IgG titer at various time points analyzed by ELISA. Pre-immune+3×SD is shown by solid horizontal lines. ELISA readings with sera dilutions, 1 month post primary immunization (filled square), 1 month post first boost (filled triangle) and 1 month post second boost (filled diamond) are shown with ±SD for individual baboons (Pan 3104, Pan 3140, Pan 3163, Pan 3275, Pan 3313). (c) Distribution of anti-Pfs48/45 IgG1(solid diamonds) and IgG2 (open diamonds) subtypes in 1 month post primary immunization sera (December 10), 1 month post 1st boost (January 10), 1 month post 2nd boost (March 06), and 3 months post 2nd boost (May 5). Data are presented as mean OD405 value±SD for individual baboon.

A group of 5 baboons (ranging 7.6 to 12.2 kg in body weight) were immunized with 50 μg of CH-rPfs48/45 in Montanide ISA-51, water-in-oil emulsion. Our choice of the adjuvant for these studies was dictated, in part, by the fact that the adjuvant has already been in use as an investigational adjuvant in clinical trials in humans [25] and that the CH-rPfs48/45 vaccine formulated in Montanide ISA-51 was strongly effective in murine immunization studies (above). The vaccine, dose, route and schedules selected were based on experience with numerous other malaria vaccine trials in nonhuman primates [26,27,28]. Here, the vaccine was delivered through the intramuscular route (quadriceps, two sites) and boosted twice with the same dose of protein at 4 and 12 weeks post primary immunization [FIG. 4a].

Figure 4B:
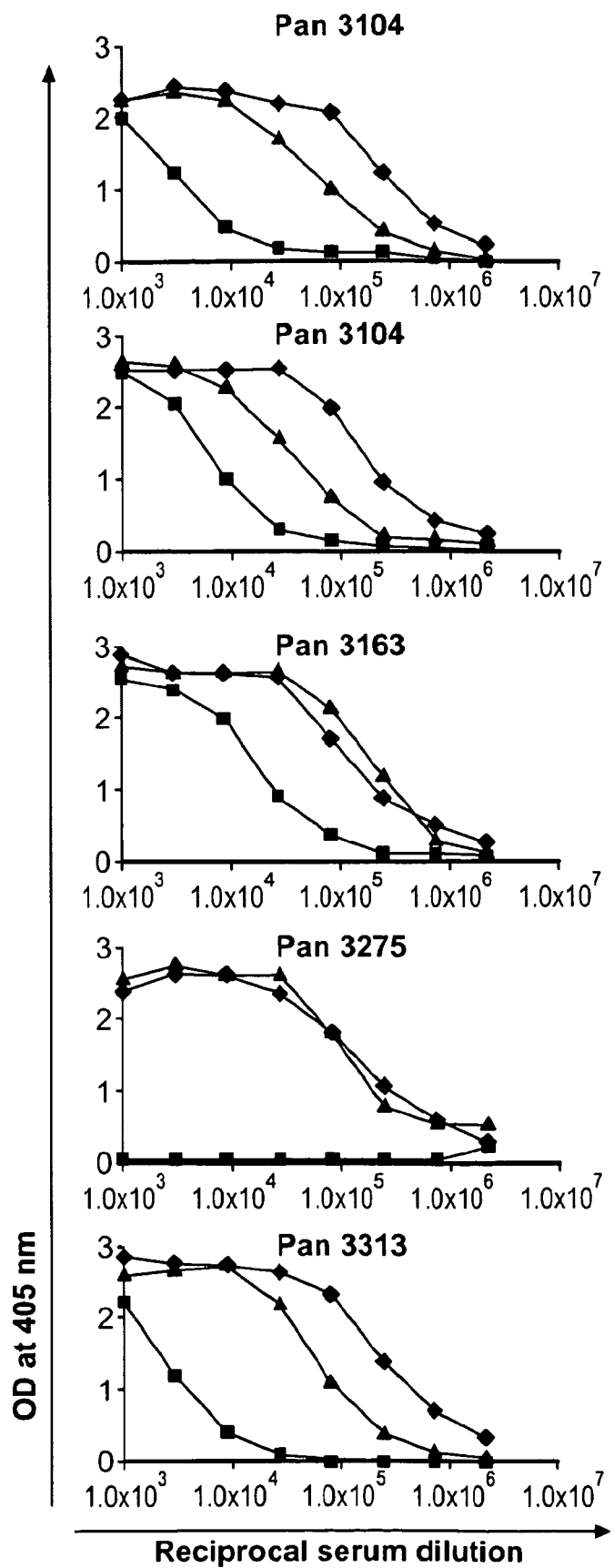
Figure 4C:
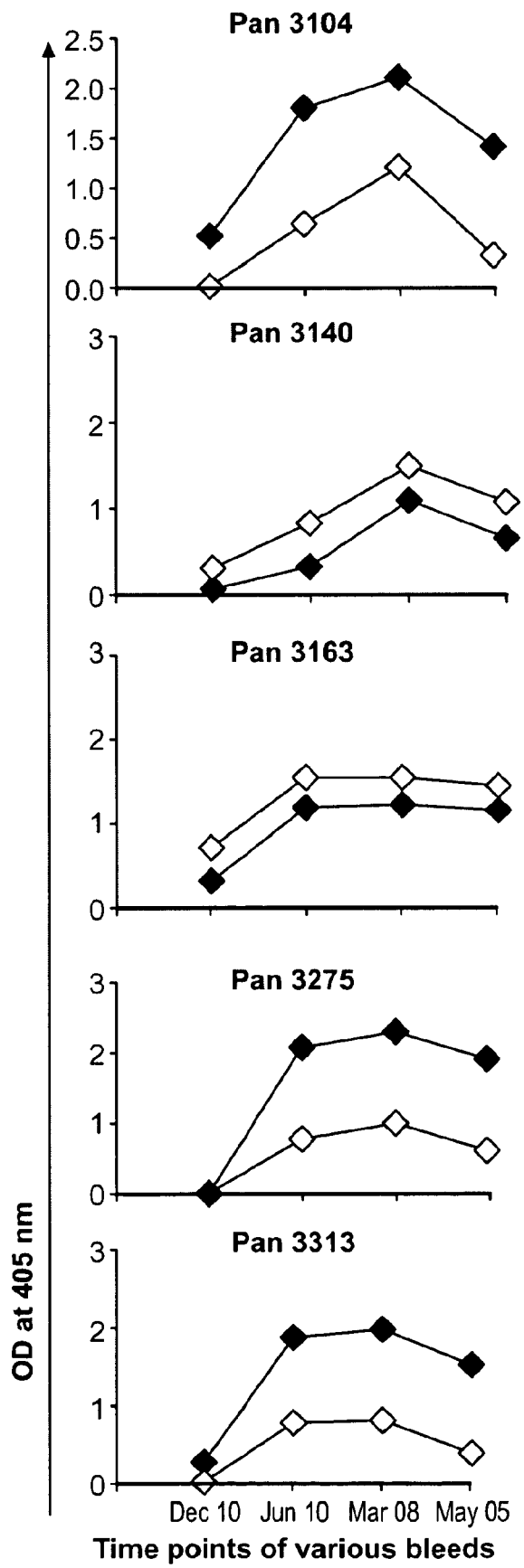

To evaluate the immunogenicity of CH-rPfs48/45 in baboons, blood samples were collected from the immunized animals and assessed by ELISA. All, except one animal (Pan 3275), responded strongly after the primary immunization showing more than 8×10^4 IgG titers 1 month after primary immunization. The titers increased to >1 million, 1 month after the first dose of booster, even in the case of the single primary dose unresponsive animal [FIG. 4b], reaching an antibody titer of more than 2 million following the second booster injection. The IgG subtypes were also tested with various bleeds. Three out of five animals showed predominantly IgG1 compared to IgG2, and for the other two animals, the reverse was the case [FIG. 4c]. IgG3 was totally absent from immunized sera in all the bleeds tested.

Mosquito MFA showed strong transmission blocking activity by all animals for various bleeds obtained at different time points post immunization [Table 2, shown below].

Pre-immune sera from each animal were used as a measure of 100% transmission for the corresponding test sera. Pre-immune serum from one animal (Pan 3275) exhibited ~30% reduced transmission when compared with the pre-immune sera of other four baboons. It is possible that natural infection by other *Plasmodium*-like parasites, such as *Enteropoides* and *Hepatocystis* spp might elicit partly cross-reactive and inhibitory activity. The average transmission blocking activity increased to greater than 97% in all the animals after a booster dose. In order to titrate the blocking effectiveness of immune sera from these animals, sera obtained one month after the second boost were further tested at various dilutions (1:4, 1:8, 1:16) in MFA. While exhibiting strong blocking activity at 1:4 and 1:8 dilutions, the sera at 1:16 dilution were still able to reduce transmission (ranging from 74% to 86%).

Figure 5:
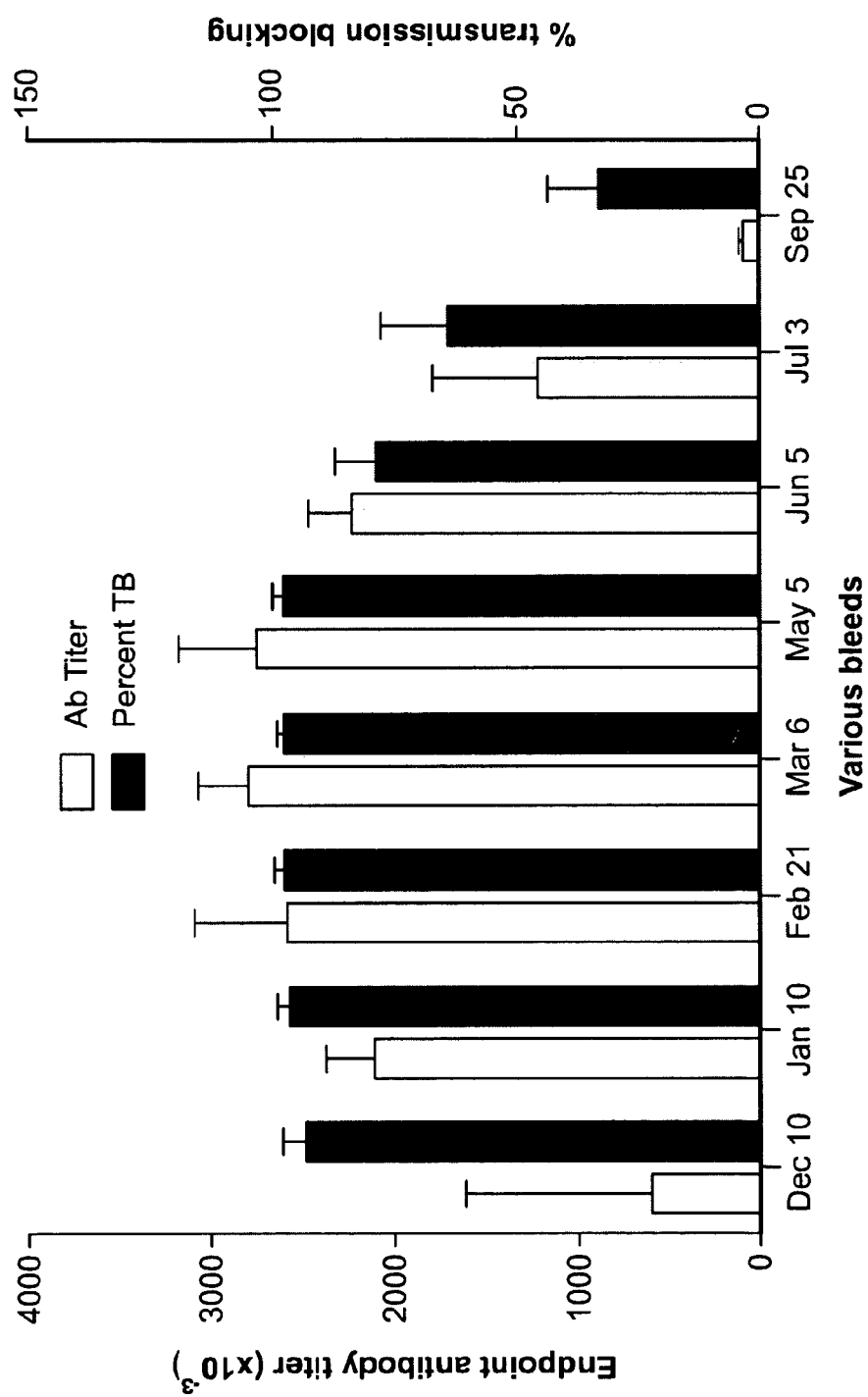
FIG. 5 is a graph that shows follow up of immune responses elicited by CH-rPfs48/45 in baboons. Analysis of anti-CH-rPfs48/45 IgG titers (open bars) and percent transmission blocking activity (closed bars) up to 7 months post second boost in baboons. Results show mean antibody titer and mean transmission blocking activity of 5 baboons+95% CI.

After the second booster dose, all five animals were bled at monthly intervals and sera analyzed for antibody titers by ELISA and functional transmission blocking activity in MFA. As shown in FIG. 5, high antibody titers and high transmission blocking activities were maintained for more than 7 months suggesting further long lasting nature of immune responses elicited by CH-rPfs48/45 in nonhuman primates.

The data reported herein shows for the very first time the expression of full length soluble recombinant Pfs48/45 protein in proper conformation with high yield following application of the codon harmonization approach for recoding gene sequences. The recombinant protein (designated CH-rPfs48/45) showed remarkable immunogenicity and functional activity, i.e. transmission blocking activity in mice immunized in the three adjuvant formulations tested. Further significance of the results is reflected by evidence from pre-clinical vaccine testing in nonhuman primates. The vaccine revealed potent immunogenicity and effective blocking activity even after a single immunization which became much stronger (approaching 100% reduction) after a booster immu-

TABLE 2

| | Bleeds [% transmission blocking * (infected/total mosquito)] | | | | |
|---|---|---|---|---|---|
| Animals | Dec. 10, 2007 | Jan. 10, 2008 | Feb. 21, 2008 | Mar. 06, 2008 | May 05, 2008 |
| Pan 3104 | 92.8 (14/27) | 95.7 (11/25) | 98.7 (6/22) | 97.7 (7/27) | 98.8 (4/19) |
| Pan 3140 | 94.4 (14/21) | 97.3 (12/28) | 98.1 (6/24) | 98.4 (7/23) | 97.8 (7/18) |
| Pan 3163 | 98.1 (5/19) | 98.5 (5/18) | 97.3 (9/27) | 97.3 (7/20) | 97.4 (11/24) |
| Pan 3275 | 88.1 (12/20) | 95.3 (11/25) | 96.2 (10/28) | 96.2 (9/23) | 97.6 (5/22) |
| Pan 3313 | 91.8 (13/25) | 97.0 (9/24) | 94.7 (13/27) | 97.8 (8/20) | 95.3 (12/24) |

*$P < 0.0001$ (Mann-Whitney test)

Table 2 shows transmission blocking activity of sera of different bleeds at various time points from baboons immunized with CH-rPfs48/45 in Montanide ISA-51. MFA was done with sera collected on Dec. 10, 2007 (1 mo post primary immunization), Jan. 10, 2008 (1 mo post 1st boost, Feb. 21, 2008 (15 d post 2nd boost), Mar. 6, 2008 (1 mo post 2nd boost), and May 5, 2008 (3 mo post 2nd boost). The geometric mean of oocyst numbers/midgut in the presence of individual pre-immune sera were 22.24 (Pan 3104), 18.43 (Pan 3140), 22.1 (Pan 3163), 6.31 (Pan 3275), and 19.7 (Pan 3313), respectively. Numbers within parenthesis represent total number of infected mosquitoes/total number of mosquitoes dissected for each feed.

Even after primary immunization, the sera (at 1:2 dilution) were capable of impressive transmission blocking with more than 93% average reduction in the number of oocysts in comparison to pre-immune sera of corresponding animal.

nization. Ease of expression and purification of protein at high yields, conformational folding and strong immunogenicity of CH-rPfs48/45 in mice and non human primates provide a much needed rationale for moving ahead with the development of malaria TBV based on Pfs48/45 antigen. Mosquito infection (oocyst load and percent infected mosquitoes) in the presence of 4/5 pre-immune sera were comparable to those obtained with normal human serum negative control.

Expression of *P. falciparum* proteins in heterologous hosts is especially challenging due to high A/T content within protein coding genes (>80%). All previous attempts to express properly folded full length recombinant Pfs48/45 have remained unsuccessful. As reported herein, codon harmonization was used to express Pfs48/45 in *E. coli* in a functionally correct conformation. Another important consideration for the development of a transmission blocking vaccine is the production of proteins in correctly folded conformation. The results herein report a robust expression of Pfs48/45 after codon harmonization of the coding sequence, the purified protein was found to be in correct conformation as revealed by Western blot analysis using monoclonal antibodies directed against reduction-sensitive conformational epitopes. The recombinant Pfs48/45 was recognized by the same antibodies even after treatment with reducing agents, suggesting that the target epitopes in the expressed proteins are stable and not susceptible to reduction.

Further development of a transmission blocking vaccine based on Pfs48/45 is supported by the observation that the purified protein exhibited very strong and longer lasting functional immunogenicity in baboons. The antibodies elicited by vaccination continued to effectively suppress, even 5-6 months after the last booster immunization, infectivity (both oocyst burden and percentage of mosquitoes infected) of *P. falciparum* gametocytes in *Anopheles* mosquitoes. Previous studies have shown that Pfs48/45 proteins normally expressed in the erythrocytic gametocyte stage of the parasite is also a target of partially effective natural immune response. It has been hypothesized that a vaccine induced response could be further boosted during natural infection and thus help in maintaining higher antibody levels in the vaccinated people.

Methods

The invention was performed with, but not limited to, the following methods and materials.

Cloning, Expression and Purification of CH-rPfs48/45

The codon harmonized sequence of Pfs48/45 containing 6× Histidines at N-terminal end was synthesized by Retrogen Inc. and cloned into the expression vector pET(K-) in *E. coli* BL21 (DE3) competent cells (Invitrogen Corp.). The cells containing pET(K-)Pfs48/45 were grown overnight at 30° C. in LB media containing 1% glucose and 50 µg/ml Kanamycin. The overnight culture was diluted 100 fold into 1 l culture in above mentioned media and grown at 30° C. with agitation until the OD600 of the culture reached 1.00. The cells were then induced with 0.1 mM of IPTG and grown for 3 h at 30° C. The cells were then harvested and centrifuged at 3800×g at 4° C. for 20 min. The pellet was kept at −80° C. for further processing. The frozen pellet was resuspended in 1×PBS (pH 7.4) at a pellet to buffer ration of 1:10 (w/v) and was lysed by microfluidization (Model M110Y, Microfluidics). The lysate was centrifuged at 24000×g for 45 min at 4° C. The lysate pellet was resuspended in 1×PBS containing 1% Tween-80 (final v/v), extracted for 30 min at 22° C. and centrifuged at 24000×g for 30 min at 4° C. The pellet was resuspended in 1×PBS containing 0.5% Sodium Lauroyl Sarcosine (sarcosyl) (final v/v), extracted and centrifuged as before. The supernatant was then passed through Ni-NTA agarose column (QIAGEN) according to manufacturer's protocol. The protein was eluted as 1 ml fractions with 1 M imidazole in 1×PBS as elution buffer. The protein was dialyzed against 1×PBS (pH 7.4) containing 10% glycerol and 0.2% Tween-80. Finally, the protein content was estimated using BCA™ Protein Assay kit (Pierce) and the endotoxin level in the protein was measured using QCL-1000 Endpoint chromogenic LAL assay kit (Lonza).

Characterization of CH-rPfs48/45

The CH-rPfs48/45 was characterized by Western blot analysis. Briefly, samples from each purification step described above were run on SDS-PAGE and transferred to nitrocellulose membrane (Bio-Rad). The membrane was blocked overnight with 1×PBS containing 5% non-fat dry milk and 0.1% Tween-20 (blocking buffer) at 4° C. Following blocking, the membrane was washed with 1×PBS containing 0.1% Tween-20 (wash buffer) and incubated with either 6×His mAb (Clontech) at 1:1000 dilution [FIG. 1*d, e*] or IIC5B10 mAb (MR4) at 1:5000 dilution [FIG. 1*f*] for 1 h at 22° C. The membrane was washed 4× in wash buffer for 30 min at 22° C. and incubated with HRP-conjugated anti-mouse IgG mAb (GE Healthcare) at 1:10000 dilution in blocking buffer for 1 h at 22° C. This was followed by washing 4× with wash buffer and ECL Plus chemiluminescent substrate (GE Healthcare) was used as detection reagent.

Immunization of Mice

Groups (n=5) of female BALB/c mice were immunized with 10 µg of CH-rPfs48/45 emulsified in either Complete Freund's Adjuvant (CFA) (Sigma) or Montanide ISA-51 (SEPPIC) or mixed in aluminum hydroxide (Alhydrogel, Brenntag) adjuvant through the intraperitoneal route. The mice immunized in CFA were boosted at 4 week intervals twice with the same quantity of protein in incomplete Freund's adjuvant. Mice in the other adjuvant groups were boosted at 4 week intervals thrice in Montanide ISA-51 or Alum, respectively. Groups of control mice were immunized with adjuvant formulations only. Blood was collected on day 0 (Pre-immune sera) and 4 weeks after primary immunization and 2 weeks post each boost for analysis of anti-Pfs48/45 IgG titer.

Immunization of Olive Baboons (*Papio anubis*)

The vaccine trial in baboons was approved by the institutional and scientific review committee of the Institute of Primate Research with a protocol #Oct. 10, 2007. Because these animals were trapped from their wild habitats, they were quarantined for 3 months and screened for the presence of any worms and protozoan parasites and successfully treated appropriately, if found infected, prior to initiating vaccination. Moreover, animals were also screened by three intradermal tuberculin tests and found to be negative for mycobacterial infections. Detailed hematological tests were also administered on all five animals during their quarantine period, just prior to and at the termination of the vaccine trial, and were certified to be in excellent health at all time points with no observable trial-related effects. A group of five baboons (ranging 7.6 to 12.2 kg in body weight) were immunized with 50 µg of CH-rPfs48/45 in Montanide ISA-51, water-in-oil emulsion. The animals were sedated with ketamine (10 mg/kg) for immunization and blood collection as per the schedule described in FIG. 4*a*.

ELISA

To assess the immunogenicity of CH-rPfs48/45, ELISA was done. Briefly, Immulon-2 plates were coated with 1.5 µg/ml CH-rPfs48/45 in carbonate-bicarbonate buffer (pH 9.6) overnight at 4° C., blocked with 5% milk in PBS and incubated with various dilutions of sera at 37° C. for 1 h. The plates were washed 5 times in PBS-0.05% Tween-20 (PBST) followed by further incubation with 1:10000 dilution of horseradish peroxidase conjugated anti-mouse IgG antibody for 1 hour at 37° C. After washing in PBST, wells were developed using ABTS substrate (Kirkegaard & Perry Laboratories Inc.) for 20 min at 22° C. and read at 405 nm in the ELISA reader. Anti-Pfs48/45 whole IgG end point titers were calculated from the highest group mean reciprocal serum dilution greater than the mean plus 3 standard deviations OD reading of pooled pre-immune sera in each assay. For IgG subtype analysis, mouse sera were tested at a single 1:1000 dilution. Various isotype-specific secondary antibodies used were anti-mouse IgG1, IgG2a, IgG2b and IgG3 from Kirkegaard & Perry Laboratories Inc.

The ELISA with baboon sera was done following a similar protocol and endpoint titers were calculated using the same criteria. The secondary antibody was anti-human IgG1, IgG2, and IgG3 conjugated to peroxidase (The Binding Site, Birmingham, UK) and used at 1:5000 dilution. Various sera were tested at 1:5000 dilution for IgG subclass analysis.

Parasite

*Plasmodium falciparum* NF54 parasites were maintained using normal red blood cells and normal human serum (O+ve blood group) as s described [32]. Stage V gametocytes were used in live IFA studies and membrane feeding assays. To extract gametocytes for Western blot analysis, the gametocyte culture was centrifuged at 1000×g for 5 min at 22° C. The RBC was lysed with 0.15% saponin in PBS for 5 min at 22° C. The gametocytes were collected after centrifugation at 1800×g for 5 min and washed thrice in 1×PBS. The gametocytes were resuspended in 25 mM Tris-Cl (pH 7.5) containing 150 mM NaCl and 1× protease inhibitor cocktail and kept frozen at −70° C. till use.

Live IFA

The gametocytes were harvested from 19 day culture and gametes were produced by incubating the gametocytes in exflagellation buffer and purified by discontinuous Nycodenz gradient centrifugation as described previously [33]. Extracellular gametes were incubated at 4° C. with 1:100 to 1:1000 dilution of immune murine sera for 60 min. Parasites were washed 3 times with 1% BSA in PBS followed by incubation with FITC-anti mouse antisera (Alexa fluor 488), 1:500 dilution at 4° C. for 60 minutes. After washing, cells were examined by upright fluorescent Nikon E800 microscope (Japan) at 100× magnification.

Membrane Feeding Assay

To test the transmission blocking activity, the murine and baboon immune sera were mixed with cultured *P. falciparum* (NF54) stage V gametocytes, normal red blood cells and normal human sera (donor blood group: O+) and fed to *Anopheles gambiae* (starved for 5-6 hours) mosquitoes through water jacketed glass membrane (stretched parafilm) feeders [10,33] Briefly, washed human red blood cells and cultures containing stage V gametocytes were resuspended to 66% hematocrit and 0.3% gametocytemia in normal human serum and maintained throughout at 37° C. Fifty microliters of various test sera (appropriately diluted in normal human sera) were mixed with 150 µl of resuspended gametocyte mix and quickly added to individual membrane feeders placed on top of cups containing starved mosquitoes. The mosquitoes were allowed to engorge for 15 min. The unfed mosquitoes were separated within 1 h of feeding and blood fed mosquitoes (typically 25-30 per cup) were maintained in the insectary at 26° C. at 80% relative humidity. In certain cases the total number of blood fed mosquites was less than 25 due to poor feeding. Moreover, a small number of blood fed mosquites (less than 5%) did not survive 9-10 days incubation period prior to dissection. Midguts were dissected 9-10 days after blood meal for enumeration of oocysts after staining with 1% mercurochrome. Transmission blocking activity of individual sera was calculated as percentage of reduction in oocyst number per midgut with test sera in comparison with pooled pre-immune sera (pre-immune murine or baboon sera was taken as allowing 100% transmission).

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

REFERENCES 1. (2008) WHO: World Malaria Report.
2. Snow R W, Guerra C A, Noor A M, Myint H Y, Hay S I (2005) The global distribution of clinical episodes of *Plasmodium falciparum* malaria. Nature 434: 214-217.
3. Greenwood B M, Fidock D A, Kyle D E, Kappe S H, Alonso P L, et al. (2008) Malaria: progress, perils, and prospects for eradication. J Clin Invest 118: 1266-1276.
4. Gosling R D, Ghani A C, Deen J L, von Seidlein L, Greenwood B M, et al. (2008) Can changes in malaria transmission intensity explain prolonged protection and contribute to high protective efficacy of intermittent preventive treatment for malaria in infants? Malar J 7:54.
5. Vekemans J, Ballou W R (2008) *Plasmodium falciparum* malaria vaccines in development. Expert Rev Vaccines 7: 223-240.
6. Bejon P, Lusingu J, Olotu A, Leach A, Lievens M, et al. (2008) Efficacy of RTS,S/AS01E vaccine against malaria in children 5 to 17 months of age. N Engl J Med 359: 2521-2532.
7. Abdulla S, Oberholzer R, Juma O, Kubhoja S, Machera F, et al. (2008) Safety and immunogenicity of RTS,S/AS02D malaria vaccine in infants. N Engl J Med 359: 2533-2544.
8. Carter R, Mendis K N, Miller L H, Molineaux L, Saul A (2000) Malaria transmission-blocking vaccines—how can their development be supported? Nat Med 6: 241-244.
9. Dimopoulos G, Kafatos F C, Waters A P, Sinden R E (2002) Malaria parasites and the *anopheles* mosquito. Chem Immunol 80: 27-49.
10. Kumar N (2007) A vaccine to prevent transmission of human malaria: a long way to travel on a dusty and often bumpy road. Curr Sci 92: 1535-1544.
11. Kaslow D C (2002) Transmission-blocking vaccines. Chem Immunol 80: 287-307.
12. Wu Y, Ellis R D, Shaffer D, Fontes E, Malkin E M, et al. (2008) Phase 1 trial of malaria transmission blocking vaccine candidates Pfs25 and Pvs25 formulated with montanide ISA 51. PLoS ONE 3: e2636.
13. Gerloff D L, Creasey A, Maslau S, Carter R (2005) Structural models for the protein family characterized by gamete surface protein Pfs230 of *Plasmodium falciparum*. Proc Natl Acad Sci USA 102: 13598-13603.
14. van Dijk M R, Janse C J, Thompson J, Waters A P, Braks J A, et al. (2001) A central role for P48/45 in malaria parasite male gamete fertility. Cell 104: 153-164.
15. Roeffen W, Lensen T, Mulder B, Teelen K, Sauerwein R, et al. (1995) A comparison of transmission-blocking activity with reactivity in a *Plasmodium falciparum* 48/45-kD molecule-specific competition enzyme-linked immunosorbent assay. Am J Trop Med Hyg 52: 60-65.
16. Outchkourov N S, Roeffen W, Kaan A, Jansen J, Luty A, et al. (2008) Correctly folded Pfs48/45 protein of *Plasmodium falciparum* elicits malaria transmission-blocking immunity in mice. Proc Natl Acad Sci USA 105: 4301-4305.

17. Komar A A, Lesnik T, Reiss C (1999) Synonymous codon substitutions affect ribosome traffic and protein folding during in vitro translation. FEBS Lett 462: 387-391.
18. Kimchi-Sarfaty C, Oh J M, Kim I W, Sauna Z E, Calcagno A M, et al. (2007) A "silent" polymorphism in the MDR1 gene changes substrate specificity. Science 315: 525-528.
19. Angov E, Hillier C J, Kincaid R L, Lyon J A (2008) Heterologous protein expression is enhanced by harmonizing the codon usage frequencies of the target gene with those of the expression host. PLoS ONE 3: e2189.
20. Darko C A, Angov E, Collins W E, Bergmann-Leitner E S, Girouard A S, et al. (2005) The clinical-grade 42-kilodalton fragment of merozoite surface protein 1 of *Plasmodium falciparum* strain FVO expressed in *Escherichia coli* protects *Aotus nancymai* against challenge with homologous erythrocytic-stage parasites. Infect Immun 73: 287-297.
21. Hillier C J, Ware L A, Barbosa A, Angov E, Lyon J A, et al. (2005) Process development and analysis of liver-stage antigen 1, a preerythrocyte-stage protein-based vaccine for *Plasmodium falciparum*. Infect Immun 73: 2109-2115.
22. Rener J, Graves P M, Carter R, Williams J L, Burkot T R (1983) Target antigens of transmission-blocking immunity on gametes of *plasmodium falciparum*. J Exp Med 158: 976-981.
23. Kumar N, Carter R (1984) Biosynthesis of the target antigens of antibodies blocking transmission of *Plasmodium falciparum*. Mol Biochem Parasitol 13: 333-342.
24. Carter R, Graves P M, Keister D B, Quakyi I A (1990) Properties of epitopes of Pfs 48/45, a target of transmission blocking monoclonal antibodies, on gametes of different isolates of *Plasmodium falciparum*. Parasite Immunol 12: 587-603.
25. Peek L J, Middaugh C R, Berkland C (2008) Nanotechnology in vaccine delivery. Adv Drug Deliv Rev 60: 915-928.
26. Collins W E, Barnwell J W, Sullivan J S, Nace D, Williams T, et al. (2006) Assessment of transmission-blocking activity of candidate Pvs25 vaccine using gametocytes from chimpanzees. Am J Trop Med Hyg 74: 215-221.
27. Wu Y, Przysiecki C, Flanagan E, Bello-Irizarry S N, Ionescu R, et al. (2006) Sustained high-titer antibody responses induced by conjugating a malarial vaccine candidate to outer-membrane protein complex. Proc Natl Acad Sci USA 103: 18243-18248.
28. Stewart V A, McGrath S M, Walsh D S, Davis S, Hess A S, et al. (2006) Pre-clinical evaluation of new adjuvant formulations to improve the immunogenicity of the malaria vaccine RTS,S/AS02A. Vaccine 24: 6483-6492.
29. Penny M A, Maire N, Studer A, Schapira A, Smith T A (2008) What should vaccine developers ask? Simulation of the effectiveness of malaria vaccines. PLoS ONE 3: e3193.
30. Guerra C A, Gikandi P W, Tatem A J, Noor A M, Smith D L, et al. (2008) The limits and intensity of *Plasmodium falciparum* transmission: implications for malaria control and elimination worldwide. PLoS Med 5: e38.
31. Roberts L (2008) Infectious disease. New malaria plan called ambitious by some, unrealistic by others. Science 322: 26-27.
32. Ifediba T, Vanderberg J P (1981) Complete in vitro maturation of *Plasmodium falciparum* gametocytes. Nature 294: 364-366.
33. Quakyi I A, Carter R, Rener J, Kumar N, Good M F, et al. (1987) The 230-kDa gamete surface protein of *Plasmodium falciparum* is also a target for transmission-blocking antibodies. J Immunol 139: 4213-4217.
34. Aguilar, J. G., and Rodriguez, E. G. (2007) Vaccine adjuvants revisited. Vaccine 25, 3752-3762
35. Sesardic, D., anoDobbelaer, R. (2004) European union regulatory developments for new vaccine adMtants and delivery systems. Vaccine 22, 2452-2456
36. Peek, L. J. et al., (2008) Nanotechnology in vaccine delivery. Advanced Drug Delivery Reviews.
37. Pink, J. R., and Kieny, M. P. (2004) 4th meeting on Novel Adjuvants Currently in/close to Human Clinical Testing World Health Organization—organisation Mondiale de la Sante Fondation Merieux, Annecy, France, 23-25, June 2003. Vaccine 22, 2097-2102
38. Lindblad, E. B. (2004) Aluminium adjuvants—in retrospect and prospect. Vaccine 22, 3658-3668.
39. Aucouturier, J., et al. (2006) The use of oil adjuvants in therapeutic vaccines. Vaccine 24, 44-45

---

What is claimed is:

1. A method for preparing a codon harmonized Pfs48/45 antigen sequence encoded by a pre-fertilization gene comprising:
   Determining the frequency of codon usage of the pre-fertilization gene coding sequence, wherein the Pfs48/45 sequence corresponding to the nucleic acid sequence represented by SEQ ID NO: 7;
   Substituting codons in the coding sequence of SEQ ID NO: 7 with codons of similar frequency from a host cell which code for the Pfs48/45 antigen, thereby preparing a codon harmonized Pfs48/45 antigen sequence wherein the codon harmonized Pfs48/45 sequence comprises the nucleotide sequence of SEQ ID NO: 2.

2. An isolated codon harmonized nucleotide sequence that comprises the nucleotide sequence of SEQ ID NO: 2 prepared according to the method of claim 1.

3. A vector comprising a codon harmonized Pfs48/45 sequence suitable for expression in a cell, wherein the codon harmonized Pfs48/45 sequence comprises the nucleotide sequence of SEQ ID NO: 2.

4. A cell expressing the vector of claim 3.

5. A kit comprising
   an immunogenic composition comprising one or more *Plasmodium falciparum* or *Plasmodium vivax* pre-fertilization or post-fertilization antigens, and instructions for use in reducing transmission of *Plasmodium falciparum* or *Plasmodium vivax*,
   together with one or more of the isolated codon harmonized nucleotide sequence comprising SEQ ID NO 2 and/or the vector of claim 3.

* * * * *